United States Patent
Nan et al.

(10) Patent No.: US 9,643,941 B2
(45) Date of Patent: May 9, 2017

(54) 2,2'-TANDEM DITHIAZOLE COMPOUND, PREPARATION METHOD THEREFOR, AND USE THEREOF

(71) Applicant: SHANGHAI INSTITUTE OF MATERIA MEDICA, CHINESE ACADEMY OF SCIENCES, Shanghai (CN)

(72) Inventors: Fajun Nan, Shanghai (CN); Jia Li, Shanghai (CN); Xin Xie, Shanghai (CN); Chaojun Gong, Shanghai (CN); Yubo Zhou, Shanghai (CN); Hui Chai, Shanghai (CN); Yangming Zhang, Shanghai (CN); Mingbo Su, Shanghai (CN)

(73) Assignee: SHANGHAI INSTITUTE OF MATERIA MEDICA, CHINESE ACADEMY OF SCIENCES, Shanghai (CN)

( * ) Notice: Subject to any disclaimer, the term of this patent is extended or adjusted under 35 U.S.C. 154(b) by 0 days.

(21) Appl. No.: 15/301,763

(22) PCT Filed: Mar. 27, 2015

(86) PCT No.: PCT/CN2015/075247
§ 371 (c)(1),
(2) Date: Nov. 4, 2016

(87) PCT Pub. No.: WO2015/149656
PCT Pub. Date: Oct. 8, 2015

(65) Prior Publication Data
US 2017/0044119 A1    Feb. 16, 2017

(30) Foreign Application Priority Data
Apr. 4, 2014 (CN) .......................... 2014 1 0136196

(51) Int. Cl.
| | |
|---|---|
| *C07D 277/56* | (2006.01) |
| *C07D 417/04* | (2006.01) |
| *C07D 417/14* | (2006.01) |
| *C07D 277/66* | (2006.01) |
| *C07D 277/60* | (2006.01) |

(52) U.S. Cl.
CPC ......... *C07D 277/56* (2013.01); *C07D 277/60* (2013.01); *C07D 277/66* (2013.01); *C07D 417/04* (2013.01); *C07D 417/14* (2013.01)

(58) Field of Classification Search
CPC ... C07D 277/56; C07D 417/04; C07D 417/14
See application file for complete search history.

(56) References Cited

FOREIGN PATENT DOCUMENTS

| | | |
|---|---|---|
| CN | 1322719 A | 11/2001 |
| CN | 101939319 A | 1/2011 |
| CN | 102775368 A | 11/2012 |
| WO | 2011116663 A1 | 9/2011 |
| WO | 2012152208 A1 | 11/2012 |

OTHER PUBLICATIONS

Saha et al., "HATs and HDACs in neurodegeneration: a tale of disconcerted acetylation homeostasis", Cell Death and Differentiation (2006) 13, 539-550.
Zain, "Role of Histone Deacetylase Inhibitors in the Treatment of Lymphomas and Multiple Myeloma", Hematol Oncol Clin N Am 26 (2012) 671-704.
Karagiannis et al., "Will broad-spectrum histone deacetylase inhibitors be superseded by more specific compounds?", Leukemia (2007) 21, 61-65.
Dinarello et al., "Histone Deacetylase Inhibitors for Treating a Spectrum of Diseases Not Related to Cancer", Mol Med 17 (5-6) 333-352, May-Jun. 2011.
Faraco et al., "The Therapeutic Potential of HDAC Inhibitors in the Treatment of Multiple Sclerosis", Mol Med 17 (5-6) 442-447, May-Jun. 2011.
International Search Report for International Application No. PCT/CN2015/075247 mailed Jul. 20, 2015.

*Primary Examiner* — Laura L. Stockton
(74) *Attorney, Agent, or Firm* — Carter, DeLuca, Farrell & Schmidt, LLP

(57) ABSTRACT

The present invention relates to a thiazole-based compound, a preparation method therefor, and a use thereof. More specifically, the present invention relates to a 2,2'-bis-thiazole-based compound, a preparation method therefor, and a use of 2,2'-bis-thiazole-based compound a histone deacetylase inhibitor in the preparation of an antitumor medicament, a medicament for treating autoimmune diseases, a medicament for treating type II diabetes mellitus and complication thereof, or a medicament for treating neurodegenerative diseases.

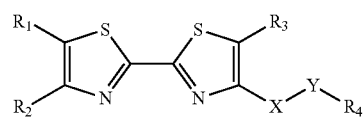

9 Claims, 1 Drawing Sheet

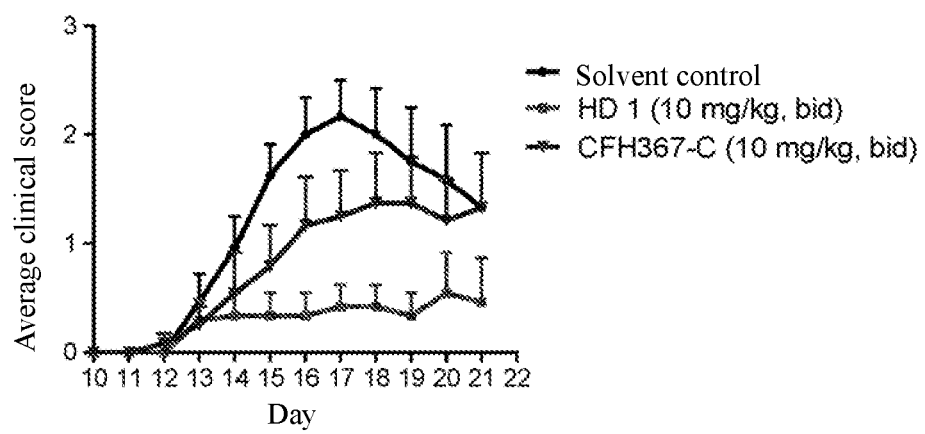
The clinical scoring for EAE mouse model

2,2'-TANDEM DITHIAZOLE COMPOUND, PREPARATION METHOD THEREFOR, AND USE THEREOF

CROSS REFERENCE TO RELATED APPLICATIONS

This application is a national stage application of International Application No. PCT/CN2015/075247, filed Mar. 27, 2015, which claims the benefit of and priority to Chinese Patent Application No. 201410136196.7, filed Apr. 4, 2014.

TECHNICAL FIELD

The present invention relates to a thiazole-based compound, preparation method therefor and the use thereof, specifically, to a 2,2'-bis-thiazole-based compound, preparation method therefor and the use of the 2,2'-bis-thiazole-based compound as a histone deacetylase inhibitor in the preparation of a medicament for anti-tumor or treating autoimmune diseases.

BACKGROUND OF THE INVENTION

Apparent-genetics, also known as pseudo-genetics, epigenetics, ex-genetics and metagenetics, is a biology discipline that investigates the reversible, heritable changes in gene function in case of the DNA sequences of a cell nucleus are not changed. It refers to the functional modification of the genome without changing the nucleotide sequence. Epigenetic phenomena include DNA methylation, RNA interference, tissue protein modification, and so on.

The post-transcription modification of histone mainly includes acetylation, methylation, phosphorylation, polyubiquitination and SUMO acylation of the histone, in which acetylation is one method that is studied most widely. Acetylation and deacetylation of histone play a key role in the process of structural modification of nuclear chromatin, which are regulated by the activities of histone acetyltransferase (HAT) and histone deacetylase (HDAC) (Saha, R. N. Pahan, K., *Cell Death Differ* 2006, 13 (4), 539-50).

Up to date, 18 human HDACs have been found and identified, and they are divided into four classes based on their similarity to yeast HDAC. The classes are type I (HDAC 1, 2, 3 and 8), type II (IIa: HDAC 4, 5, 7 and 9, IIb: HDAC 6 and 10), and type IV (HDAC 11), the activity of all these types depend on $Zn^{2+}$. For type III HDACs (SirT 1-7), the enzyme activity depends on $NAD^+$. (Karagiannis, T. C., El-Osta, A. Leukemia 2007, 21(1), 61-5.)

The histone deacetylase inhibitors (HDACi) involves in the regulation of the following important biological functions, including: 1) inducing apoptosis through exogenous or intrinsic apoptosis mechanisms; 2) blocking cell cycle; 3) inhibiting the neovascularization; 4) acetylation of tubulin and destruction of aggregate formation; 5) changing the tubulin structure to affect cell motility and differentiation; 6) regulating tumor immunity by the way of influencing the function of T cell receptors, the cytokine environment of immune effector cells, and directly up-regulating the other immune effector to identify the tumor cell protein, etc. (Zain J., Hematol Oncol Clin Northam, 2012, 26 (3): 671-704.) HDAC dysfunction may lead to imbalance of histone acetylation, so as to change the chromatin structure, and make the cell growth, differentiation, and apoptosis-related gene expression be inhibited, and finally lead to tumor formation. Currently, HDAC is an important target for the development of new antitumor drugs. In 2006, FDA approved SAHA (Vorinostat) as the first marketed HDACi for the treatment of cutaneous T-cell lymphoma (CTCL). In 2009, FK228 was marketed as a drug for treating CTCL and peripheral T-cell lymphoma (PTCL).

Recent studies have shown that HDACi may also be associated with a variety of autoimmune diseases. Early in 2003, Pahan et al. reported that HDAC inhibitor sodium phenylbutyrate can alleviate the central nervous system injury in the animal models of multiple sclerosis (MS) mice (experimental autoimmune encephalomyelitis, EAE), but did not explain the direct relationship between this result and the HDAC; two years later, Camelo et al. found that HDACi TSA can effectively inhibit the invasion of T cells to the mice central nervous system, he stressed that because of the inhibition of TSA against HDAC, the expression of neuroprotective protein such as IGF-2 and glutamate transporter EAAT2 and so on was increased, and thus a therapeutic effect was achieved; then there are many researchers who found the application of HDACi to MS, e.g., the studies of Ryu et al. showed that selective HDACi can increase the acetylation of the transcription factor Sp1 to protect the neuronal cells survival against oxidative stress (Giuseppe Faraco, et al., *Molecular Medicine,* 2011, 17 (5-6), 442-447). In view of the unknown mechanism of MS and the lack of sensitive diagnostic markers currently, HDACi may actively promote the treatment of MS. In addition, according to the report (Charles A Dinarello, et al., *Molecular Medcine,* 2011, 17(5-6), 333-352), HDACi is also associated with type 2 diabetes and its associated complications, neurodegenerative diseases (Huntington's disease, Alzheimer's disease) and so on, so HDAC is a target with a good research prospects.

The currently studied HDAC inhibitors mainly comprise three moieties: a chelating moiety with $Zn^{2+}$ (ZBG), a hydrophobic linking moiety (Linker) and a surface recognition structural domain. According to the various zinc ion chelating groups, they can be divided into hydroximic acids, o-phenylenediamines, electron-deficient ketones, short-chain fatty acids and so on. According to the data from Thomson Reuters in December 2013, there are more than 100 HDACi being at different stages of drug research and development. The first listed SAHA is the hydroxypentanoic acid HDAC inhibitor which is used in the treatment of CTCL. With the further use, its shortcomings are exposed: the treatment effect of single drug is only average, it is not the first-line drug, the toxicity in high doses is obvious, and accompanied by the side effect of prolonged QT interval, bone marrow suppression, diarrhea and so on, and the treatment effect on solid tumor is not desired. This may be due to the fact that SAHA is a pan-inhibitor, and probably because it contains a strong zinc-ion chelating group, i.e., hydroximic acid group. Therefore, it is an important research direction in the art to develop newer and more efficient HDAC inhibitors.

The inventors of the present application filed a patent application (WO2012152208) in 2012, and reported a novel thiazole-based compound which can be used as HDAC inhibitors for the development of anti-tumor and multiple sclerosis drugs. In which, the compound CFH367-C showed good enzymatic inhibition activity, GI50 on HCT-116 cell was less than 1 μM, and the clinical symptoms of EAE mice were effectively relieved. However, due to the shortcomings of hydroxamic acid groups, it is desirable to develop a more active, less toxic HDAC inhibitor.

Based on the basic structure of the HDAC inhibitor, the inventors started from replacing the zinc ion chelating group (ZBG), firstly, the hydroxamic acid in the CFH367-C was replaced with the common o-phenylenediamine, but the obtained compounds has the enzyme level of $IC_{50}$ decreased from 60 nM to 2-5 μM. After replacing the ZBG with a trifluoromethyl ketone and even no reported hydrazone compounds, the zinc ion chelating ability was reduced, however, it was unexpectedly found that these compounds has a higher enzyme inhibition activity ($IC_{50}$=30 nM), a more inhibitory activity at the cellular level (IC50 up to 100 nM), and the treatment effect on clinical symptoms in EAE mice is significantly better than CFH367-C (the FIGURE), which shows a better development prospect.

SUMMARY OF THE INVENTION

It is an object of the present invention to provide a 2,2'-bis-thiazole-based compound having a structure represented by the following formula I:

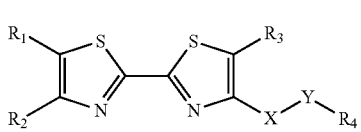

Formula I wherein:

$R_1$ and $R_2$ are each independently one selected from the group consisting of H, $C_3$-$C_6$ cycloalkyl, $C_1$-$C_6$ alkyl, $C_2$-$C_6$ alkenyl, $C_2$-$C_6$ alkynyl; or $R_1$ and $R_2$ form a 5- to 7-membered cyclic structure together with the carbon atoms to which they are attached;

Preferably, $R_1$ and $R_2$ are each independently H or $C_1$-$C_6$ alkyl, or $R_1$ and $R_2$ form a 5-, 6- or 7-membered saturated cyclic structure together with the carbon atoms to which they are attached;

X is

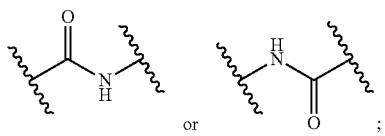 [SMILES: *NC(*)=O ; *NC(*)=O]

Y is

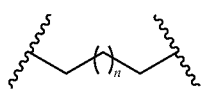

or $C_2$-$C_6$ alkenylene, wherein n is 1, 2, 3 or 4; more preferably, Y is

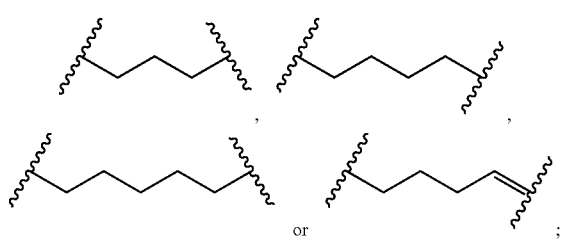

$R_3$ is one selected from the group consisting of H, $C_1$-$C_6$ alkyl, $C_1$-$C_6$ alkyl substituted with $C_6$-$C_{10}$ aryl, $C_3$-$C_6$ cycloalkyl, $C_3$-$C_6$ cycloalkyl substituted with $C_1$-$C_6$ alkyl, $C_2$-$C_8$ alkenyl, $C_2$-$C_6$ alkynyl, $C_6$-$C_{10}$ aryl, 5- to 7-membered heteroaryl; said 5- to 7-membered heteroaryl contains 1 to 3 heteroatom(s) selected from N, O and S;

Preferably, $R_3$ is $C_1$-$C_4$ alkyl, $C_1$-$C_4$ alkyl substituted with $C_6$-$C_{10}$ aryl, or $C_3$-$C_6$ cycloalkyl;

More preferably, $R_3$ is $C_1$-$C_4$ alkyl, benzyl, or cyclopropyl.

$R_4$ is $R_{4a}$, $R_{4b}$, $R_{4c}$, $R_{4d}$ or $R_{4e}$:

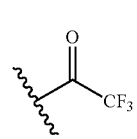 $R_{4a}$

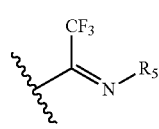 $R_{4b}$

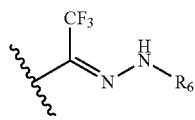 $R_{4c}$

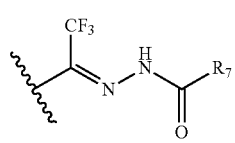 $R_{4d}$

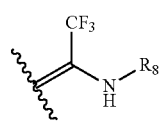 $R_{4e}$

Wherein, $R_5$, $R_6$, $R_7$ and $R_8$ are one selected from the group consisting of H, hydroxyl, $C_1$-$C_6$ alkyl, $C_1$-$C_6$ alkoxy, hydroxyl ($C_1$-$C_6$) alkylene, $C_1$-$C_6$ alkyl substituted with $C_6$-$C_{10}$ aryl, $C_3$-$C_6$ cycloalkyl, $C_3$-$C_6$ cycloalkyl substituted with $C_1$-$C_6$ alkyl, $C_2$-$C_8$ alkenyl, $C_2$-$C_6$ alkynyl, $C_6$-$C_{10}$ aryl, 5- to 7-membered heteroaryl,

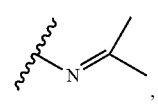 [SMILES: *N=C(C)C]

said 5- to 7-membered heteroaryl contains 1 to 3 heteroatom(s) selected from N, O and S;

Preferably, $R_5$ is hydroxyl, $C_1$-$C_6$ alkyl, $C_1$-$C_6$ alkoxy, $C_6$-$C_{10}$ aryl, or

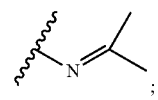 [SMILES: *N=C(C)C]

More preferably, $R_5$ is hydroxyl, $C_1$-$C_4$ alkyl, $C_1$-$C_4$ alkoxy, phenyl, or

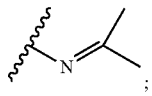
;

Preferably, $R_6$ is H or $C_1$-$C_6$ alkyl;

More preferably, $R_6$ is H or methyl;

Preferably, $R_7$ is $C_1$-$C_6$ alkyl, $C_3$-$C_6$ cycloalkyl, $C_1$-$C_6$ alkoxy, hydroxyl ($C_1$-$C_6$) alkylene, $C_6$-$C_{10}$ aryl or 5- to 7-membered heteroaryl, said 5- to 7-membered heteroaryl contains 1 to 3 heteroatom(s) selected from N, O and S;

More preferably, $R_7$ is $C_1$-$C_4$ alkyl, $C_3$-$C_5$ cycloalkyl, $C_1$-$C_4$ alkoxy, hydroxy $C_1$-$C_4$ alkylene, $C_6$-$C_{10}$ aryl or 5- to 7-membered heteroaryl, said 5- to 7-membered heteroaryl contains 1-2 heteroatom(s) selected from N, O and S (e.g., pyridine);

Most preferably, $R_7$ is methyl, ethyl, propyl, isopropyl, tert-butyl, cyclopropyl, methoxy, ethyloxy, hydroxymethyl, hydroxyethyl, phenyl, pyridinyl, pyridazinyl, pyrimidinyl or pyrazinyl;

Preferably, $R_8$ is $C_6$-$C_{10}$ aryl;

More preferably, $R_8$ is phenyl.

The exemplary 2,2'-bis-thiazole-based compounds having a structure represented by the formula I of the present invention include:

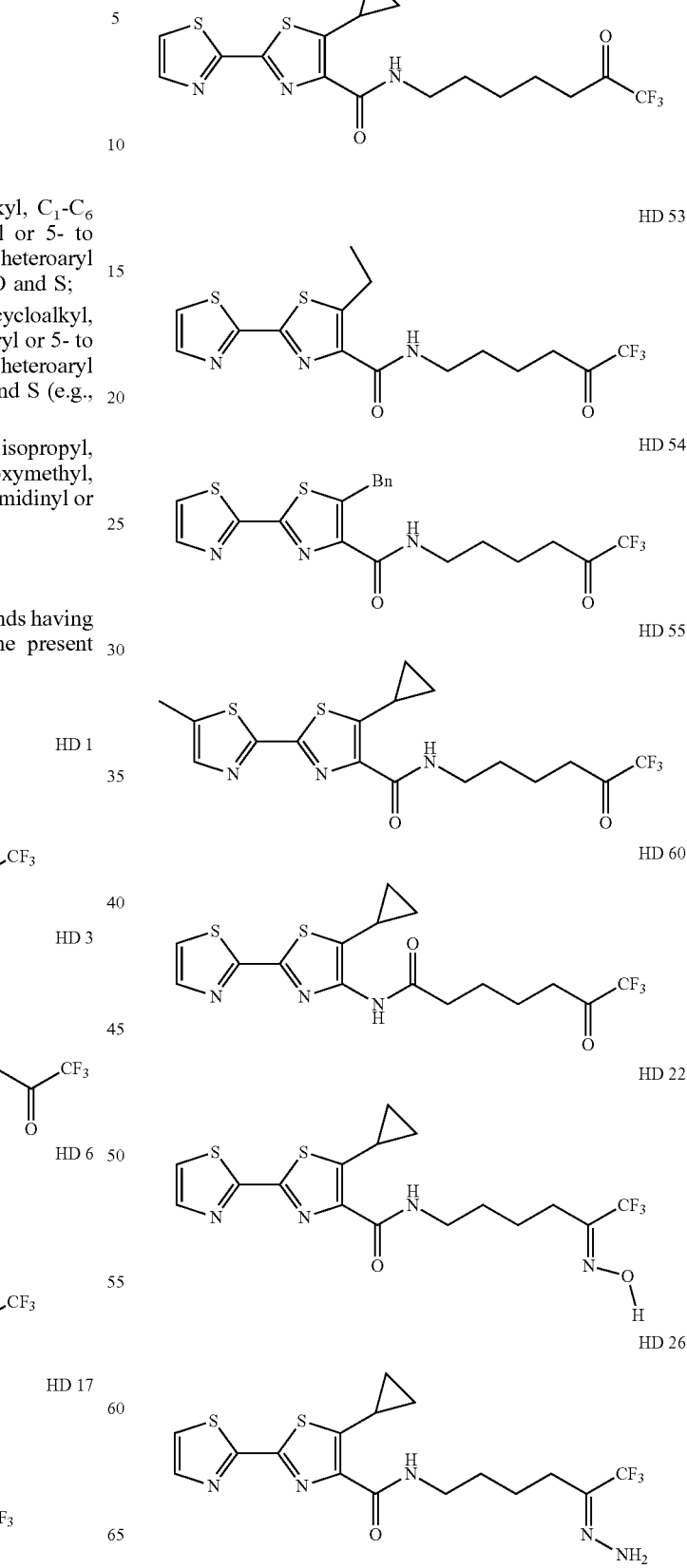

HD 27
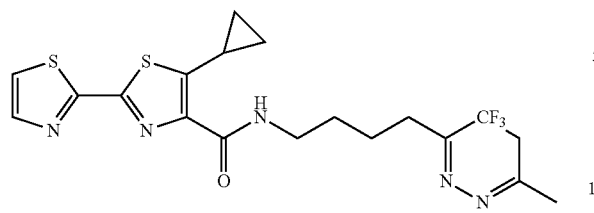
HD 32
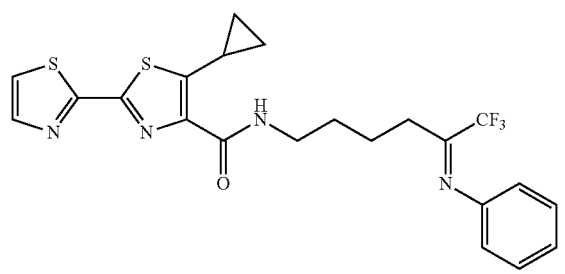
HD 33
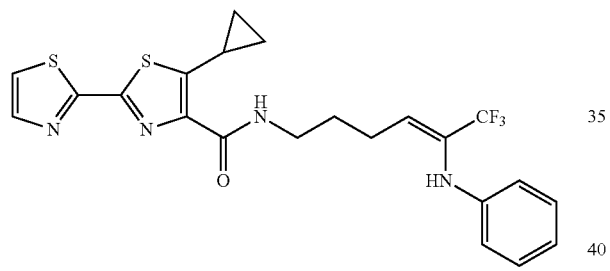
HD 45
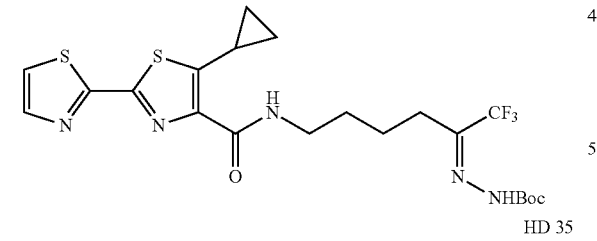
HD 35
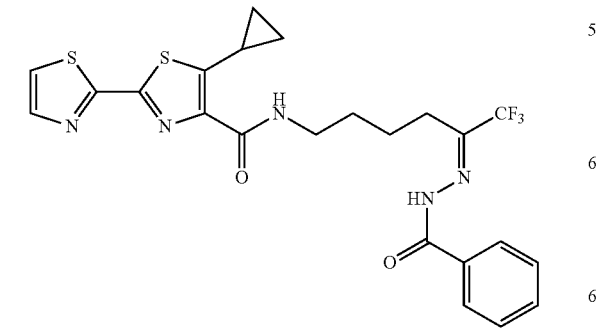
HD 36
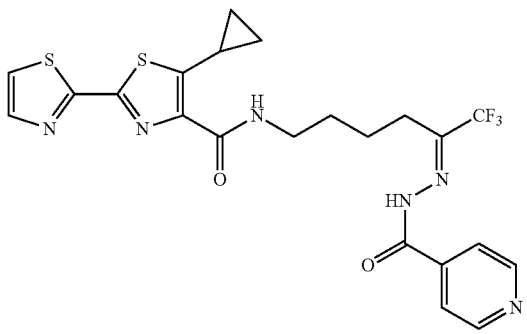
HD 40
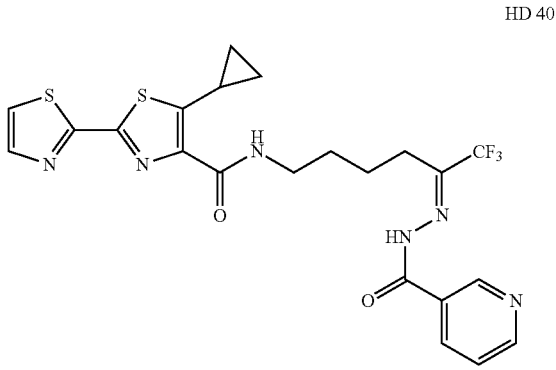
HD 41
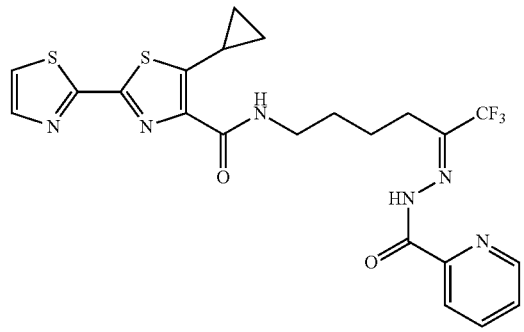
HD 37
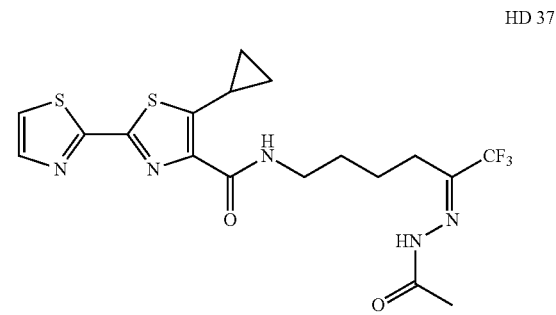

HD 46

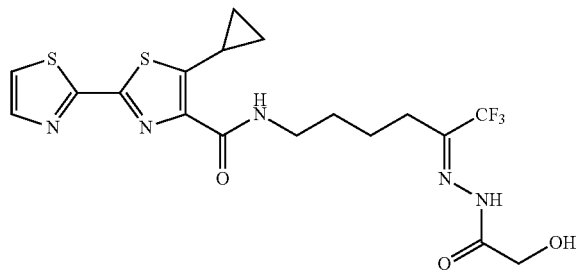

HD 48

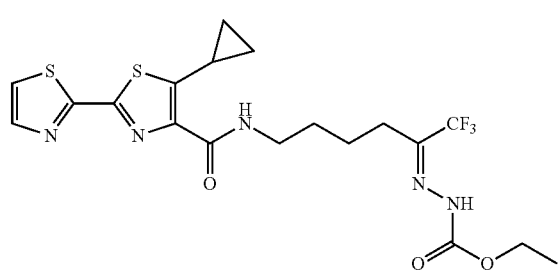

HD 49

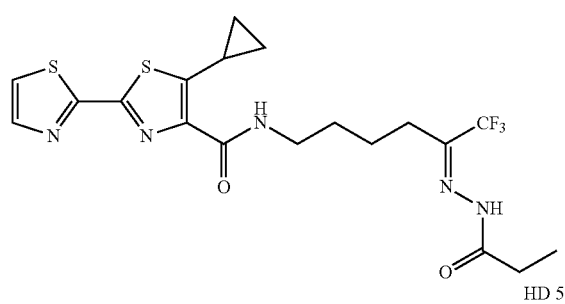

HD 50

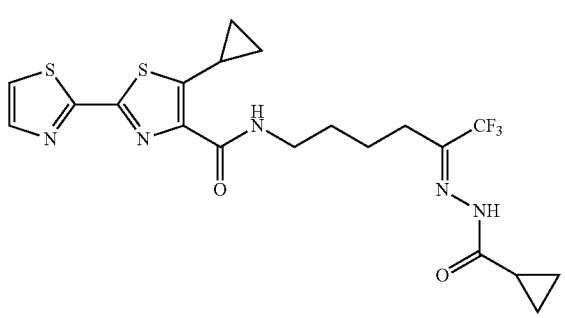

HD 51

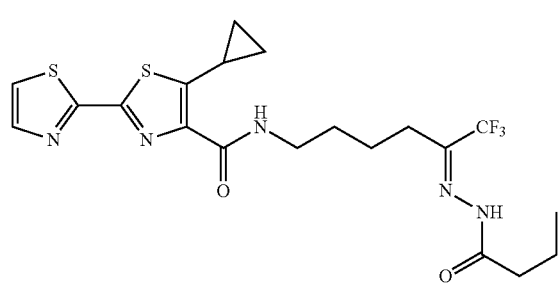

HD 52

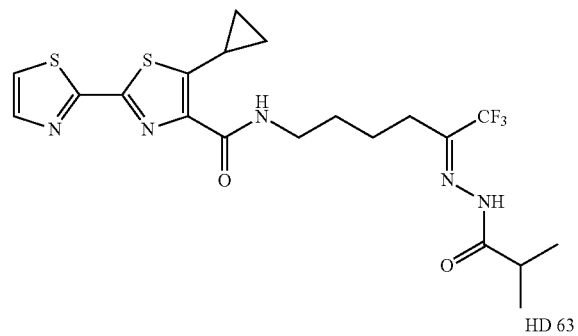

HD 63

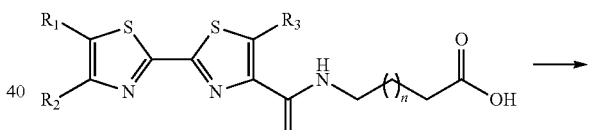

It is another object of the present invention to provide a process for preparing the 2,2'-bis-thiazole-based compound having a structure represented by the formula I.

Compounds Ia may be obtained by one of the following Route I to Route III (Compounds 1 and 2 may be prepared by the process described in WO2012152208 or WO2011116663):

Route I:

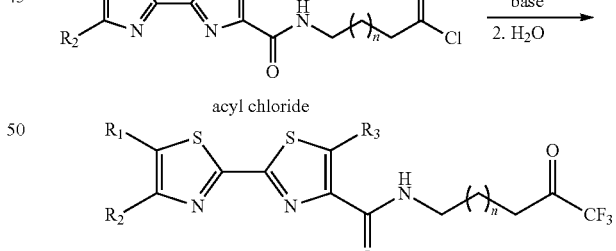

Wherein, the definitions of $R_1$, $R_2$, $R_3$ and n are the same as defined in the above formula I, Specifically, compound 1 is converted to acyl chloride using an acyl chloride reagent, such as oxalyl chloride, thionyl chloride and so on, and then the acyl chloride is subjected to a substitution reaction with trifluoroacetic anhydride (TFAA) in the presence of a base, such as pyridine, at room temperature or under heating, and then the resultant is hydrolyzed to give compound Ia;

Route II:

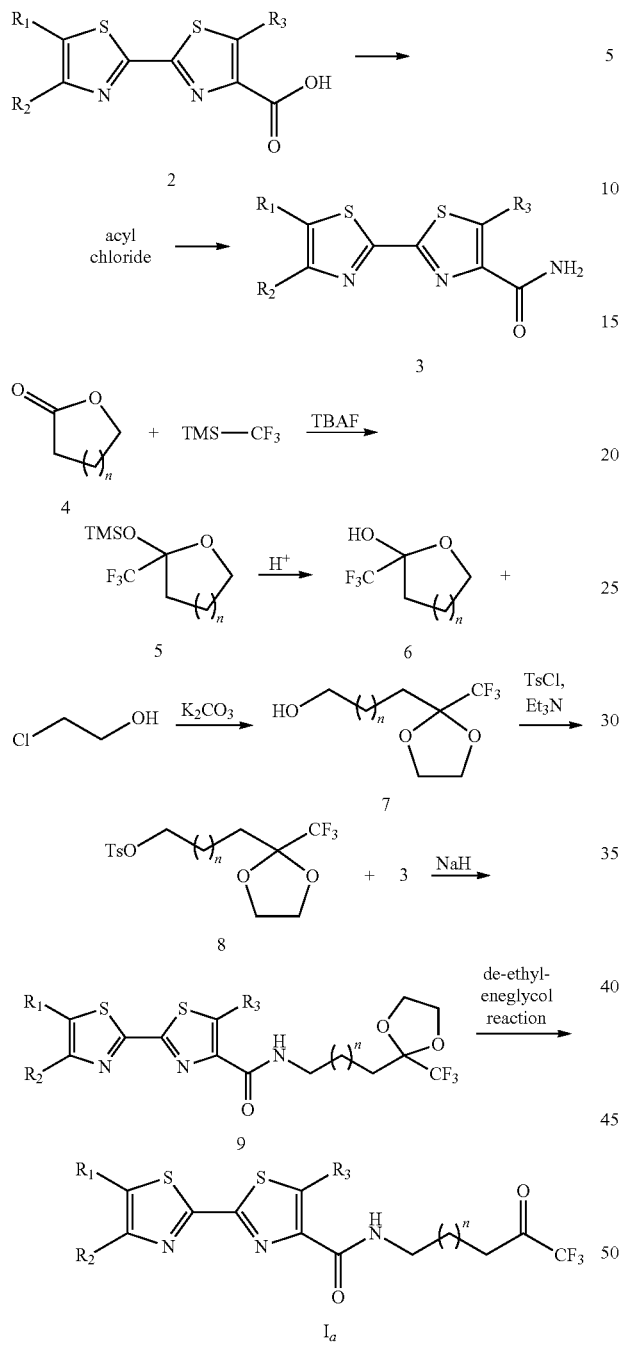

Wherein, the definitions of $R_1$, $R_2$, $R_3$ and n are the same as defined in the above formula I;

Specifically, compound 2 is converted to acyl chloride using an acyl chloride reagent, such as oxalyl chloride, thionyl chloride and so on, and then the acyl chloride is reacted with concentrated ammonia water under an ice bath to obtain compound 3;

Compound 4 is subjected to an additive reaction with (trifluoromethyl)trimethylsilane (TMS-CF$_3$) under the catalyst of tetrabutylammonium fluoride (TBAF) in tetrahydrofuran to give compound 5; compound 5 is hydrolyzed by acid (H$^+$) to give compound 6; compound 6 is reacted with 2-chloroethanol in DMF in the presence of K$_2$CO$_3$ to give compound 7; compound 7 is sulfonylated in DCM in the presence of TsCl and Et$_3$N to give compound 8; compound 8 and compound 3 are reacted under the action of sodium hydride in DMF to give compound 9; and compound 9 is subjected to de-ethyleneglycol reaction under the action of a Lewis acid (e.g., BBr$_3$) to give compound Ia;

Route III:

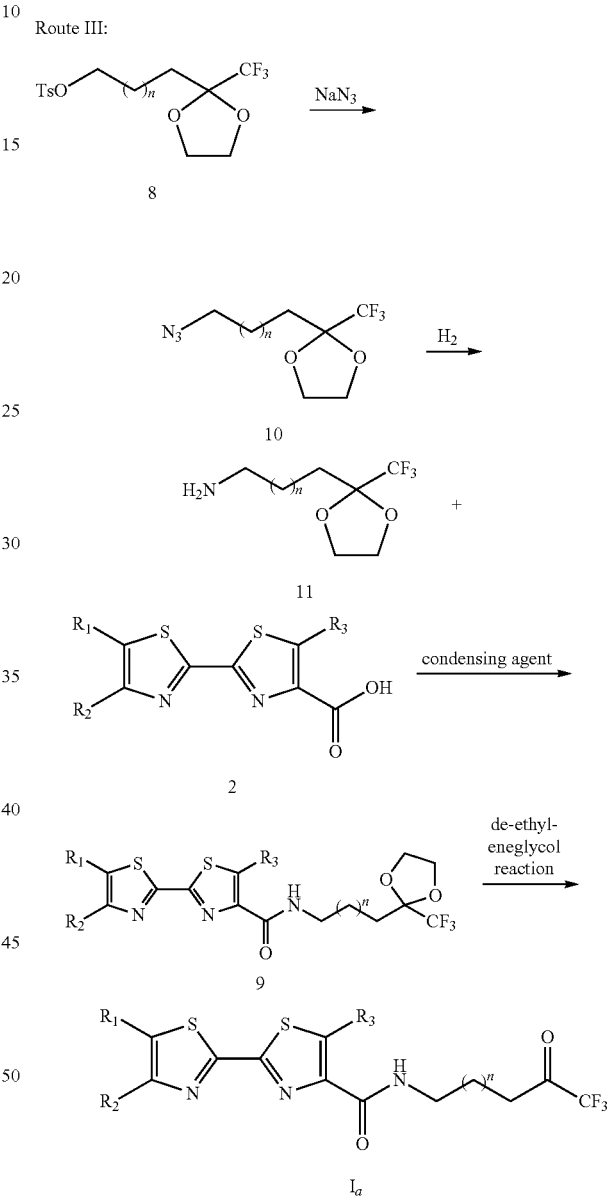

Wherein, the definitions of $R_1$, $R_2$, $R_3$ and n are the same as defined in the above formula I;

Specifically, compound 8 is reacted with sodium azide (NaN$_3$) in DMF to obtain compound 10; compound 10 is reduced by hydrogenation to give amine 11; amine 11 is subjected to condensation reaction with acid 2 in the presence of a condensing agent such as EDCI in DCM to give compound 9; compound 9 is subjected to de-ethyleneglycol reaction under the action of a Lewis acid (for example, BBr3) to give compound Ia;

Compound Ib may be prepared by route IV:

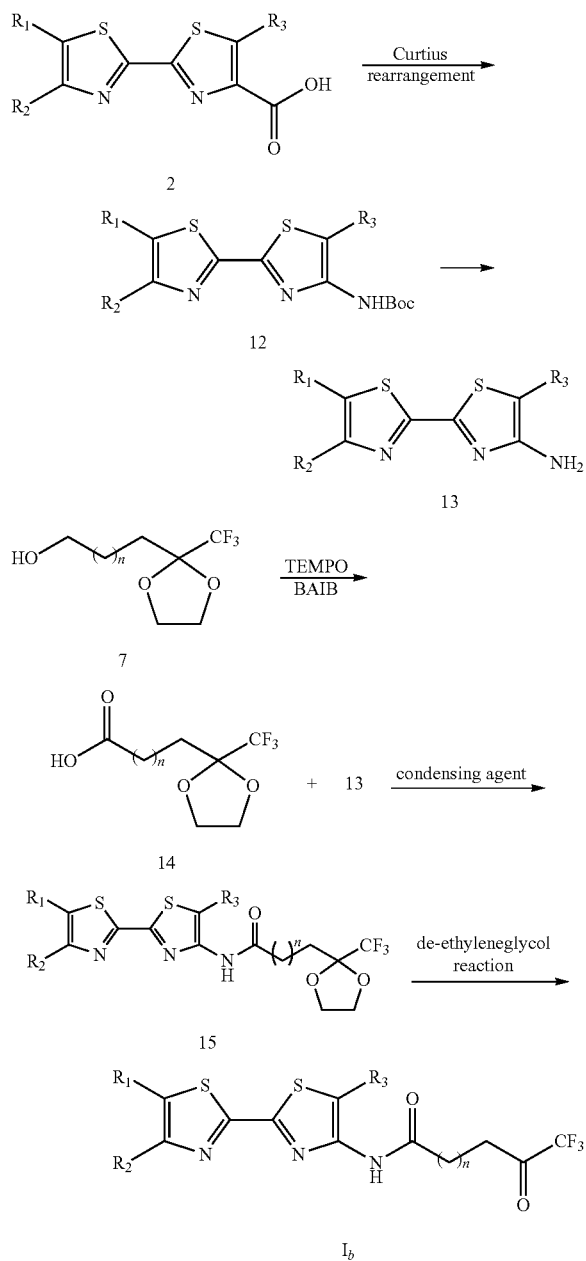

Compound Ic may be obtained by Route V:

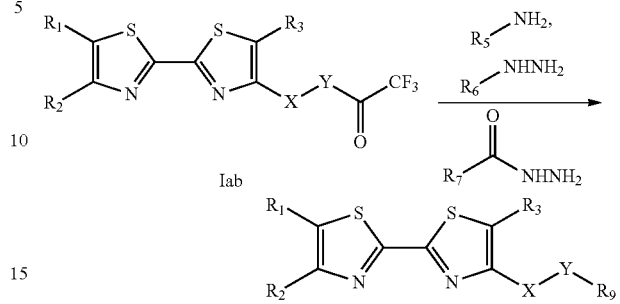

Wherein, the definitions of $R_1$, $R_2$, $R_3$ and n are the same as defined in the above formula I.

Specifically, compound 2 is subjected to Curtius rearrangement reaction to give a Boc-protected amine 12; Boc group is removed from 12 to give a free amine 13; while compound 7 is oxidized by TEMPO and iodobenzene diacetate (BAIB) to give acid 14; the acid 14 is reacted with the amine 13 under the action of the condensing agent EDCI to give compound 15; and compound 15 is subjected to de-ethyleneglycol reaction under the action of a Lewis acid (for example, BBr3) to give the thiazole-based compound Ib of the present invention;

Wherein, the definitions of $R_1$, $R_2$, $R_3$, $R_5$, $R_6$, $R_7$, X and Y are the same as defined in the above formula I.

$R_9$ is one selected from $R_{4b}$, $R_{4c}$ and $R_{4d}$.

Specifically, compound $I_{ab}$ may be subjected to a dehydration condensation reaction with the corresponding amine or hydrazine in a solvent such as ethanol, pyridine or the like at room temperature or under heating (e.g., 65° C.) to obtain the bis-thiazole-based compound Ic of the present invention.

It is another object of the present invention to provide a use of a bis-thiazole-based compound having a structure represented by the formula I in the preparation of a medicament as the histone deacetylase inhibitor, and to provide a use of a bis-thiazole-based compound having a structure represented by the formula I in the preparation of an antitumor medicament, a medicament for treating autoimmune diseases, a medicament for treating type II diabetes mellitus and complications thereof, or a medicament for treating neurodegenerative diseases, wherein the tumor is multiple myeloma, cutaneous T cell lymphoma, peripheral T cell Lymphoma and the like, and the autoimmune disease is multiple sclerosis, and the neurodegenerative disease is Huntington's disease or Alzheimer's disease, etc.

It is another object of the present invention to provide a pharmaceutical composition comprising a therapeutically effective amount of one or more selected from the group consisting of bis-thiazole-based compounds having a structure represented by the formula I and pharmaceutically acceptable excipient.

BRIEF DESCRIPTIONS OF THE DRAWINGS

The FIGURE shows a clinical score in the experiment for the drug effect of HDAC inhibitor HD1 in EAE mice.

DETAILED DESCRIPTION

The present invention will be further described with reference to specific examples, but the present invention is not limited to these examples.

PREPARATION EXAMPLES

In the following Preparation Examples, NMR was measured using Mercury-Vx 300M instrument manufactured by Varian, NMR calibration: δ H 7.26 ppm (CDCl$_3$), 2.50 ppm (DMSO-d$_6$), 3.31 ppm (CD$_3$OD); all solvents were analytical reagent, and were generally used directly without treatment. Anhydrous solvent was treated for drying according to standard method. Other reagents were generally purchased from Sinopharm Chemical Reagent Co., Ltd., Accela Chem-Bio Co., Ltd., GL Biochem (Shanghai) Ltd., Shenzhen Meryer Chemical Technology Company, Aldrich, Alfa-Aesar, Acros, Fluka, Merck, TCI or Lancaster reagents, a small number of reagents were purchased from the manufacturer, unless otherwise specified, and these reagents were directly used without treatment. In general, self-made reagents were subjected to NMR before use to determine the structure and the general purity thereof. Silica gel plate for TLC thin layer chromatography was from Huiyou Silicone Development Co., Ltd., Yantai, Shandong, model HSGF 254; Silica gel for normal phase chromatography used in the purification of compound was from Branch of Qingdao Haiyang Chemical Co., Ltd., model zcx-11, 200-300 meshes.

Preparation Example I (Compound No. HD 1-Route I)

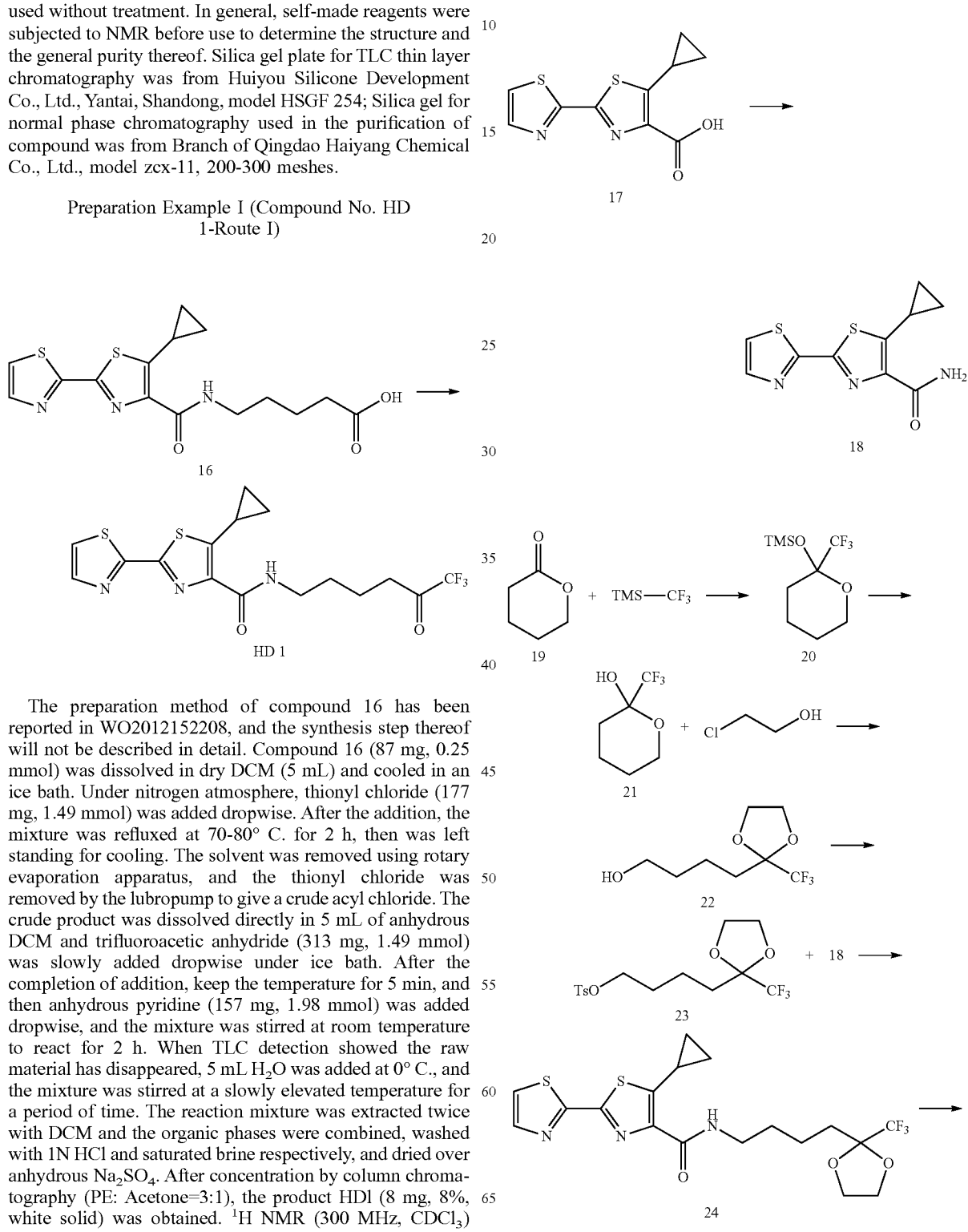

The preparation method of compound 16 has been reported in WO2012152208, and the synthesis step thereof will not be described in detail. Compound 16 (87 mg, 0.25 mmol) was dissolved in dry DCM (5 mL) and cooled in an ice bath. Under nitrogen atmosphere, thionyl chloride (177 mg, 1.49 mmol) was added dropwise. After the addition, the mixture was refluxed at 70-80° C. for 2 h, then was left standing for cooling. The solvent was removed using rotary evaporation apparatus, and the thionyl chloride was removed by the lubropump to give a crude acyl chloride. The crude product was dissolved directly in 5 mL of anhydrous DCM and trifluoroacetic anhydride (313 mg, 1.49 mmol) was slowly added dropwise under ice bath. After the completion of addition, keep the temperature for 5 min, and then anhydrous pyridine (157 mg, 1.98 mmol) was added dropwise, and the mixture was stirred at room temperature to react for 2 h. When TLC detection showed the raw material has disappeared, 5 mL H$_2$O was added at 0° C., and the mixture was stirred at a slowly elevated temperature for a period of time. The reaction mixture was extracted twice with DCM and the organic phases were combined, washed with 1N HCl and saturated brine respectively, and dried over anhydrous Na$_2$SO$_4$. After concentration by column chromatography (PE: Acetone=3:1), the product HD1 (8 mg, 8%, white solid) was obtained. $^1$H NMR (300 MHz, CDCl$_3$) δ7.85 (d, J=3.3 Hz, 1H), 7.48 (s, 1H), 7.44 (d, J=3.3 Hz, 1H), 3.49 (q, J=7.2 Hz, 2H), 3.46-3.40 (m, 1H), 2.82 (t, J=6.9 Hz, 2H), 1.81-1.73 (m, 2H), 1.72-1.62 (m, 2H), 1.37-1.28 (m, 2H), 0.81-0.77 (m, 2H). ESIMS (m/z): 426.1[M+Na$^+$]

Preparation Example II (Compound No. HD 1-Route II)

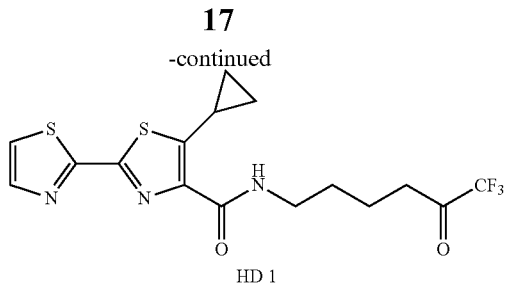

HD 1

The preparation method of compound 17 has been reported in WO2012152208, and the synthesis step thereof will not be described in detail. Compound 17 (252 mg, 1 mmol) was dissolved in 4 mL of dry THF, and 20 μL of DMF was added therein. 0.25 mL of oxalyl chloride was added dropwise at 0° C., and after the dropwise, the mixture was reacted at room temperature for 3 h. Then the mixture was cooled to 0° C. again, added with a mixed liquid of 1.5 mL of concentrated ammonia water and 4.5 mL of water, then the resultant was stirred at room temperature for 30 min and filtered to give compound 18 (118 mg, 47% as a white solid). $^1$H NMR (300 MHz, CDCl$_3$) δ7.85 (d, J=3.3 Hz, 1H), 7.44 (d, J=3.3 Hz, 1H), 7.247.19 (s, 1H), 5.54 (s, 1H), 3.49-3.33 (m, 1H), 1.37-1.32 (m, 2H), 0.85-0.79 (m, 2H), ESIMS(m/z): 274.0[M+Na$^+$];

Compound 19 (25 g, 0.25 mol) and (trifluoromethyl)trimethylsilane (39 g, 0.27 mol) were dissolved in 150 mL of dry THF. 2.7 mL of TBAF (1 M in THF) was added dropwise under nitrogen atmosphere at 0° C., followed by spontaneous warming and then the mixture was reacted at room temperature overnight. The solvent was rotatory evaporated, and the residue was distilled under reduced pressure by the lubropump. Fractions of 72-74° C. were collected to give compound 20. (46.3 g, 77%, colorless liquid) $^1$H NMR (300 MHz, CDCl$_3$) δ 3.79 (dd, J=6.4, 2.6 Hz, 2H), 1.72-1.57 (m, 6H), 0.21 (s, 9H).

Compound 20 was directly dissolved in 1N HCl solution, the mixture was stirred overnight at room temperature, extracted with diethyl ether, and dried over anhydrous Na$_2$SO$_4$, then the solvent was carefully rotatory evaporated to give compound 21, without purification. The crude compound 21 (37 g, 0.11 mol) and 2-chloroethanol (26.5 g, 0.33 mol) were dissolved in 250 mL of DMF. After stirring and reacting at room temperature for 2 h, K$_2$CO$_3$ (45.6 g, 0.33 mol) was added thereto and the reaction was carried out at room temperature overnight. The reaction liquid was diluted with a large amount of H$_2$O, and extracted with EA for three times. The organic phases were combined, washed with water and saturated brine, and dried over anhydrous Na$_2$SO$_4$. The solvent was rotatory evaporated to give compound 22 (28.8 g, 70% in two steps, colorless liquid), without purification. $^1$H NMR (300 MHz, CDCl$_3$) δ 4.15-4.11 (m, 2H), 4.11-4.07 (m, 2H), 3.64 (t, J=6.3 Hz, 2H), 2.03 (s, 1H), 1.88-1.80 (m, 2H), 1.62-1.43 (m, 4H), ESIMS(m/z): 237.1[M+Na$^+$].

Compound 22 (28 g, 0.13 mol) was dissolved in 250 mL of DCM, 4-methylbenzenesulfonyl chloride (37 g, 0.19 mol) and pyridine (20.6 g, 0.26 mol) were added thereto and the mixture was reacted overnight at room temperature. The solvent was rotatory evaporated, and the residue was dissolved in EA. The organic phase was washed with H$_2$O, 1N HCl, H$_2$O, saturated NaHCO$_3$ aqueous solution and saturated brine respectively, and then dried over anhydrous Na$_2$SO$_4$. The resultant was concentrated and subjected to column chromatograph (PE:EA=10:1-4:1) to give compound 23. (20.5 g, 43%, colorless oil) $^1$H NMR (300 MHz, CDCl$_3$) δ 7.79 (d, J=8.4 Hz, 2H), 7.35 (d, J=8.4 Hz, 2H), 4.15-4.13 (m, 2H), 4.08-4.05 (m, 2H), 4.02 (t, J=6.3 Hz, 2H), 2.45 (s, 3H), 1.79-1.62 (m, 4H), 1.48-1.45 (m, 2H), ESIMS(m/z): 391.1[M+Na$^+$].

Compound 23 (587 mg, 1.59 mmol) and compound 18 (600 mg, 2.39 mmol) were dissolved in 20 mL of dry DMF, NaH (100 mg, 2.5 mmol) was added under N$_2$ atmosphere, and then the mixture was reacted at room temperature for 3 h. When TLC detection showed Compound 23 essentially disappeared, 10 mL of 1 N HCl was added to the reaction liquid, the mixture was extracted three times with EA, and the organic phases were combined. The organic phase was washed three times with H$_2$O and saturated brine, and dried over anhydrous Na$_2$SO$_4$. The resultant was concentrated and subjected to column chromatography (PE:Acetone=6:1) to give compound 24. (266 mg, 37.5%, colorless oil) $^1$H NMR (300 MHz, CDCl$_3$) δ 7.84 (d, J=3.0 Hz, 1H), 7.45 (s, 1H), 7.43 (d, J=3.0 Hz, 1H), 4.15-4.11 (m, 2H), 4.13-4.07 (m, 2H), 3.46 (t, J=6.3 Hz, 2H), 3.42-3.39 (m, 1H), 1.93-1.85 (m, 2H), 1.72-1.67 (m, 2H), 1.56-1.50 (m, 2H), 1.34-1.27 (m, 2H), 0.83-0.79 (m, 2H), ESIMS(m/z): 470.1[M+Na$^+$].

Compound 24 (656 mg, 1.46 mmol) was dissolved in 10 mL of anhydrous DCM. 5 mL of BBr$_3$ (2N in DCM) solution was slowly added dropwise under nitrogen atmosphere at 0° C., followed by spontaneous warming and reacting. After 1 h, TLC detection showed the raw material has disappeared. The reaction solution was cooled in an ice bath, and was quenched by carefully dropping 5 mL of H$_2$O. Then the mixture was extracted with DCM, the organic phase was washed with saturated brine, dried over anhydrous Na$_2$SO$_4$, and the resultant was rotatory evaporated to give the crude product. The crude product was dissolved in 5 mL of acetone, 5 mL of 1 N HCl was added thereto, and the reaction was carried out at 50° C. overnight. After cooling, the solvent was rotatory evaporated, the mixture was adjusted with 1 N NaOH to pH~2, and a solid was precipitated. The precipitated solid was filtered and washed with a little 1 N NaOH to give the product HD1 (260 mg, 44%, white solid). $^1$H NMR was the same as above.

Preparation Example III (Compound No. HD 1-Route III)

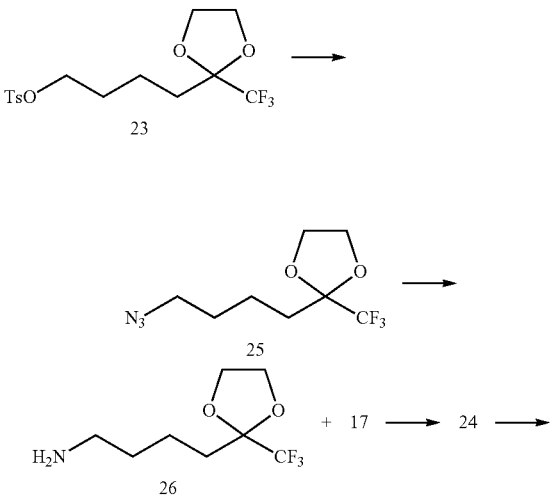

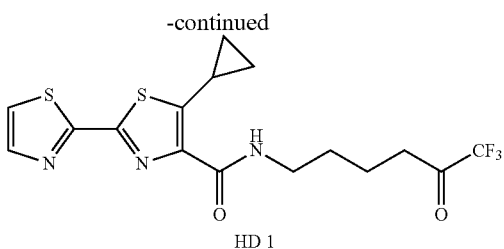

HD 1

Compound 23 (20 g, 0.054 mol) was dissolved in 200 mL of DMF, sodium azide (7 g, 0.108 mol) and K$_2$CO$_3$ (22.4 g, 0.162 mol) were added thereto, and the mixture was reacted at room temperature. After 2 h, TLC detection showed the raw material has disappeared, and the reaction liquid was added with 100 mL of H$_2$O, followed by extracted with ethyl acetate (100 mL*3). The organic phase was washed with H$_2$O (150 mL*3) and saturated brine (150 mL) respectively, dried over anhydrous Na$_2$SO$_4$. The solvent was rotatory evaporated to give compound 25 (11.9 g, 92%, colorless liquid), without purification. $^1$H NMR (300 MHz, CDCl$_3$) δ 4.20-4.14 (m, 2H), 4.13-4.09 (m, 2H), 3.29 (t, J=6.6 Hz, 2H), 1.86 (t, J=7.5 Hz, 2H), 1.66-1.58 (m, 2H), 1.56-1.48 (m, 2H).

Compound 25 (8.39 g, 0.035 mol) was dissolved in 150 mL of ethyl acetate. After replacement by N$_2$, 839 mg of a 10% palladium-carbon hydrogenation catalyst was added, followed by replacement by N$_2$ again, and finally replaced by H$_2$ for three times, then the reaction was carried out at room temperature. After 5 h, TLC detection showed the raw material has disappeared it was replaced by N$_2$ again, the mixture was filtered through celite, the filter cake was washed with ethyl acetate, and the filtrate was rotatory evaporated to give compound 26 (7.38 g, 98%, pale yellow liquid). $^1$H NMR (300 MHz, CDCl$_3$) δ 4.16-4.11 (m, 2H), 4.09-4.07 (m, 2H), 2.70 (t, J=6.3 Hz, 2H), 1.83 (t, J=7.8 Hz, 2H), 1.47 (s, 4H), ESIMS (m/z): 214.1[M+H$^+$].

Compound 17 (6.82 g, 0.027 mol) and compound 26 (7.38 g, 0.035 mol) were dissolved in 150 mL of DCM, and DMAP (4.9 g, 0.04 mol) was added thereto. After stirring for 10 min, EDCI (7.76 g, 0.04 mol) was added under ice bath, and the reaction was carried out at room temperature overnight. The organic phase was washed with 1N HCl and saturated brine respectively, and dried over anhydrous Na$_2$SO$_4$. After concentration, the resultant was subjected to the column chromatography (PE:Acetone=6:1) to give compound 24 (6.37 g, 53%) as a colorless oil. $^1$H NMR data were the same as above. The protecting group of compound 24 was removed by the method of Route II to give compound HD 1. $^1$H NMR was the same as above.

The following compound may be obtained with one of the above three routes:

| Compound | Structural formula | $^1$H NMR and MS data |
|---|---|---|
| HD 1 | | $^1$H NMR (300 MHz, CDCl$_3$) δ 7.85 (d, J = 3.3 Hz, 1H), 7.48 (s, 1H), 7.44 (d, J = 3.3 Hz, 1H), 3.49 (q, J = 7.2 Hz, 2H), 3.46-3.40 (m, 1H), 2.82 (t, J = 6.9 Hz, 2H), 1.81-1.73 (m, 2H), 1.72-1.62 (m, 2H), 1.37-1.28 (m, 2H), 0.81-0.77 (m, 2H) ESIMS (m/z): 426.1 [M + Na$^+$] |
| HD 3 | | $^1$H NMR (300 MHz, CDCl$_3$) δ 7.45 (t, J = 6.6 Hz, 1H), 3.51-3.39 (m, 3H), 2.81 (t, J = 6.6 Hz, 4H), 1.89 (t, J = 3.0 Hz, 2H), 1.83-1.75 (m, 2H), 1.75-1.66 (m, 2H), 1.32-1.25 (m, 2H), 0.86-0.77 (m, 2H) ESIMS (m/z): 480.1 [M + Na$^+$] |
| HD 6 | | $^1$H NMR (300 MHz, CDCl$_3$) δ 7.88 (d, J = 3.0 Hz, 1H), 7.53 (s, 1H), 7.45 (d, J = 3.0 Hz, 1H), 3.50-3.42 (m, 3H), 3.27 (d, J = 6.6 Hz, 2H), 2.80 (t, J = 6.6 Hz, 2H), 2.04-1.97 (m, 1H), 1.82-1.70 (m, 4H), 1.00 (d, J = 6.6 Hz, 3H) ESIMS (m/z): 432.1 [M + Na$^+$] |
| HD 17 | | $^1$H NMR (300 MHz, CDCl$_3$) δ 7.86 (d, J = 3.0 Hz, 1H), 7.49 (s, 1H), 7.44 (d, J = 3.0 Hz, 1H), 3.51 (q, J = 6.6 Hz, 2H), 3.44-3.40 (m, 1H), 2.87 (t, J = 7.2 Hz, 2H), 2.09-2.00 (m, 2H), 1.36-1.30 (m, 2H), 0.84-0.79 (m, 2H) ESIMS (m/z): 412.1 [M + Na$^+$] |

-continued

| Compound | Structural formula | ¹H NMR and MS data |
|---|---|---|
| HD 25 | | ¹H NMR (300 MHz, CDCl₃) δ 7.84 (d, J = 3.3 Hz, 1H), 7.44 (s, 1H), 7.42 (d, J = 3.3 Hz, 1H), 3.49-3.42 (m, 3H), 2.74 (t, J = 7.2 Hz, 2H), 1.79-1.63 (m, 4H), 1.50-1.40 (m, 2H), 1.36-1.29 (m, 2H), 0.84-0.77 (m, 2H) ESIMS (m/z): 440.1 [M + Na⁺] |
| HD 53 | | ¹H NMR (300 MHz, CDCl₃) δ 7.88 (d, J = 3.0 Hz, 1H), 7.46 (d, J = 3.0 Hz, 1H), 7.45 (s, 1H), 3.55-3.46 (m, 2H), 3.44-3.34 (m, 2H), 2.81 (t, J = 6.9 Hz, 2H), 1.78-1.65 (m, 4H), 1.37 (t, J = 7.5 Hz, 3H) ESIMS (m/z): 414.1 [M + Na⁺] |
| HD 54 | | ¹H NMR (300 MHz, CDCl₃) δ 7.83 (d, J = 3.0 Hz, 1H), 7.54 (s, 1H), 7.43 (d, J = 3.0 Hz, 1H), 7.35-7.28 (m, 5H), 4.73 (s, 2H), 3.50 (q, J = 6.6 Hz, 2H), 2.82 (t, J = 6.6 Hz, 2H), 1.84-1.68 (m, 4H) ESIMS (m/z): 476.1 [M + Na⁺] |
| HD 55 | | ¹H NMR (300 MHz, CDCl₃) δ 7.49 (s, 1H), 7.46 (s, 1H), 3.52-3.45 (m, 3H), 2.81 (t, J = 6.9 Hz, 2H), 2.53 (s, 3H), 1.83-1.66 (m, 4H), 1.34-1.27 (m, 2H), 0.80-0.78 (m, 2H) ESIMS (m/z): 440.1 [M + Na⁺] |

Preparation Example IV (Compound No. HD 60)

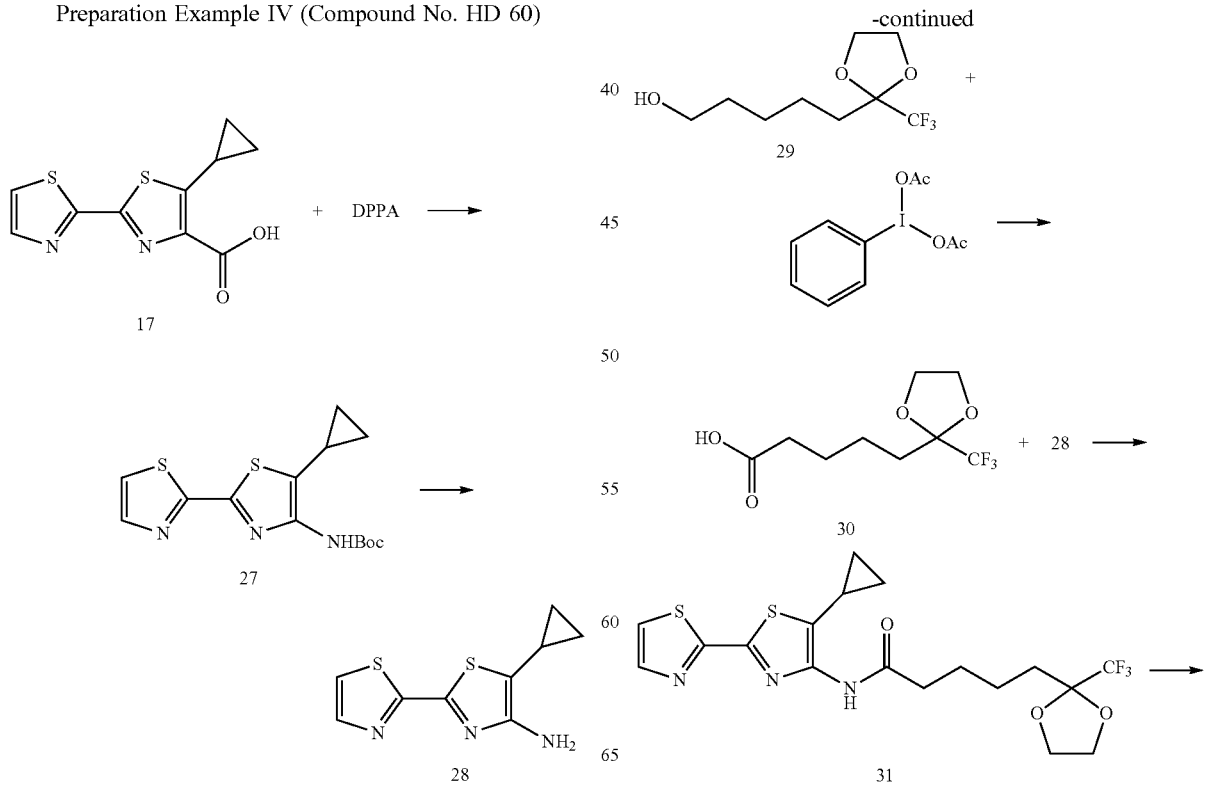

-continued

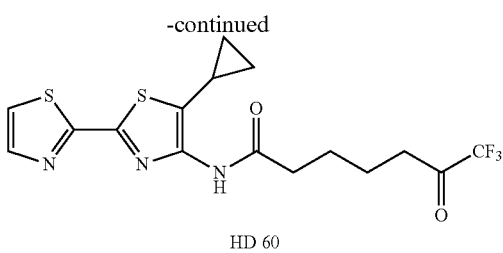

HD 60

Compound 17 (1 g, 3.96 mmol) was placed in 20 mL of t-butanol and protected with $N_2$. Triethylamine (600 mg, 5.9 mmol) and diphenylphosphoryl azide (DPPA, 1.4 g, 5.15 mmol) was added dropwise at 30° C., followed by refluxing in the dark to react overnight. The reaction liquid was cooled to room temperature, and a large amount of $H_2O$ was added thereto, then the mixture was extracted with ethyl acetate, and the organic phases were combined. The organic phase was washed with $H_2O$, saturated $NaHCO_3$ aqueous solution, 5% citric acid solution and saturated brine respectively, and then dried over anhydrous $Na_2SO_4$. The resultant was concentrated, and subjected to column chromatograph (PE: EA=10:1) to give compound 27 (245 mg, 20%, pale yellow solid). $^1H$ NMR (300 MHz, $CDCl_3$) δ 7.82 (d, J=3.0 Hz, 1H), 7.39 (d, J=3.0 Hz, 1H), 6.50 (s, 1H), 2.12-2.04 (m, 1H), 1.51 (s, 9H), 1.14 1.06 (m, 2H), 0.77-0.71 (m, 2H). ESIMS (m/z): 346.1[M+Na$^+$].

Compound 27 (90 mg, 0.278 mmol) was dissolved in 5 mL of DCM, 5 mL of 2N HCFEA solution was dropwise added thereto at 0° C., and then the mixture was allowed to spontaneously rise till room temperature to react. After 4 h, the reaction was completed as shown in TLC detection. The saturated $NaHCO_3$ solution was added thereto to adjust the pH to be alkaline, the mixture was extracted with DCM, the organic phase was washed with saturated brine, and dried over anhydrous $Na_2SO_4$. The resultant was concentrated to give compound 28 (40 mg, 65%, yellow oil). $^1H$ NMR (300 MHz, $CDCl_3$) δ 7.79 (d, J=3.3 Hz, 1H), 7.33 (d, J=3.3 Hz, 1H), 4.13 (s, 2H), 1.74-1.67 (m, 2H), 1.02-0.97 (m, 2H), 0.70-0.65 (m, 2H). ESIMS (m/z): 246.0 [M+Na$^+$].

Compound 29 (a colorless liquid) may be obtained from ε-caprolactone according to the method as described in Route II. $^1H$ NMR (300 MHz, $CDCl_3$) δ 4.19-4.13 (m, 2H), 4.11-4.05 (m, 2H), 3.65 (t, J=6.3 Hz, 2H), 1.84 (t, J=6.0 Hz, 2H), 1.63-1.54 (m, 2H), 1.45-1.36 (m, 4H).

Compound 29 (113 mg, 0.495 mmol) was dissolved in a total 2 mL solvent of $CH_3CN:H_2O=1:1$, iodobenzene diacetate (BAIB, 479 mg, 1.49 mmol) and 2,2,6,6-tetramethylpiperidine-1-oxyl radical (TEMPO, 23 mg, 0.149 mmol) were added thereto, and the mixture was allowed to react overnight at room temperature. When TLC detection showed the reactant has disappeared, 1 mL of saturated $Na_2S_2O_3$ solution was added to the reaction liquid, the mixture was extracted with ethyl acetate, the organic phase was washed with saturated brine, and dried over anhydrous $Na_2SO_4$. After concentration, the resultant was subjected to the column chromatography (PE:acetone=4:1) to give compound 30 (100 mg, 83%, near white solid). $^1H$ NMR (300 MHz, $CDCl_3$) δ 4.16-4.11 (m, 2H), 4.09-4.07 (m, 2H), 2.37 (t, J=7.5 Hz, 2H), 1.84 (t, J=7.5 Hz, 2H), 1.69-1.61 (m, 2H), 1.50-1.43 (m, 2H). ESIMS(m/z): 241.0[M−H$^+$].

Compound 28 (41 mg, 0.186 mmol) and compound 30 (45 mg, 0.186 mmol) were dissolved in DCM, DMAP (68 mg, 0.557 mmol) was added thereto, EDCI (53 mg, 0.276 mmol) was added thereto at 0° C. under $N_2$ atmosphere, then the reaction was carried out at room temperature overnight. To the reaction liquid was added $H_2O$, the mixture was extracted with ethyl acetate. The organic phase was washed with saturated brine and dried over anhydrous $Na_2SO_4$. After concentration, the resultant was subjected to the column chromatography (PE:acetone=10:1-4:1) to give compound 31 (35 mg, 42%, pale yellow solid). $^1H$ NMR (300 MHz, $CDCl_3$) δ 7.83 (d, J=3.0 Hz, 1H), 7.61 (s, 1H), 7.39 (d, J=3.0 Hz, 1H), 4.15-4.11 (m, 2H), 4.11-4.08 (m, 2H), 2.44 (t, J=6.3 Hz, 2H), 1.87-3.39 (m, 1H), 1.93-1.85 (m, 2H), 1.53-1.43 (m, 2H), 1.16-1.08 (m, 2H), 0.85-0.71 (m, 2H), 0.83-0.79 (m, 2H), ESIMS(m/z): 470.1 [M+Na$^+$].

Compound 31 was deprotected to remove the protecting group according to the method analogous to Route II to give compound HD 60 (white solid).

$^1H$ NMR (300 MHz, $CDCl_3$) δ 7.84 (d, J=3.3 Hz, 1H), 7.48 (s, 1H), 7.41 (d, J=3.3 Hz, 1H), 2.79 (s, 2H), 2.48 (s, 2H), 2.04-2.03 (m, 1H), 1.80-1.68 (m, 4H), 1.11-1.02 (m, 2H), 0.79-0.73 (m, 2H). ESIMS(m/z): 404.1[M+H$^+$].

Preparation Example V (Compound No. HD 46)

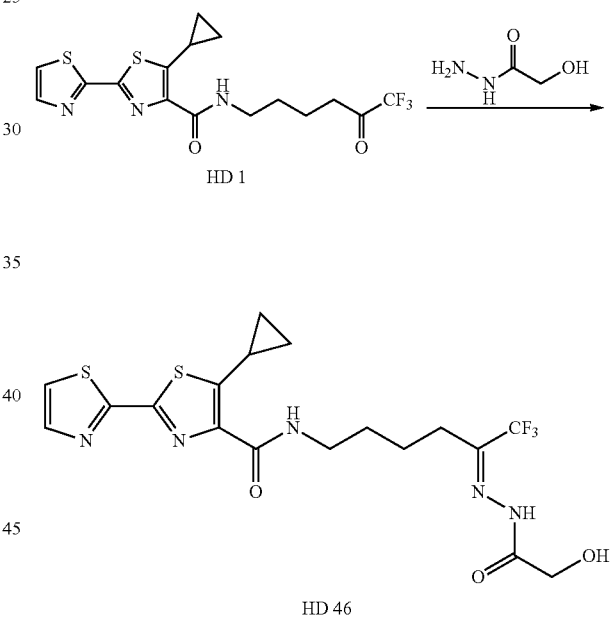

The compound GCJ403 (403 mg, 1 mmol) was dissolved in 10 mL of ethanol, hydroxyacetyl hydrazide (180 mg, 2 mmol) and 0.5 mL of glacial acetic acid were added thereto and the reaction was carried out at 65° C. overnight. The heating was stopped, after the cooling, ethanol was removed using rotary evaporation apparatus, and the residue was dissolved with ethyl acetate. The organic phase was washed with $H_2O$ and saturated brine respectively, and dried over anhydrous $Na_2SO_4$. After concentration, the resultant was subjected to the column chromatography (PE:acetone=4:1-1:1) to give compound HD 46 (275 mg, 62%, white solid). $^1H$ NMR (300 MHz, $CDCl_3$) δ 10.68 (s, 1H), 7.85 (d, J=3.3 Hz, 1H), 7.74 (s, 1H), 7.44 (d, J=3.3 Hz, 1H), 4.48 (d, J=4.5 Hz, 2H), 3.78-3.72 (m, 1H), 3.57 (dd, J=11.4, 6.6 Hz, 2H), 3.12 (s, 1H), 2.68 (t, J=8.4 Hz, 2H), 1.77-1.73 (m, 2H), 1.73-1.70 (m, 2H), 1.42-1.37 (m, 2H), 0.87-0.76 (m, 2H). ESIMS(m/z): 498.0[M+Na$^+$].

The following compounds were synthesized in the same manner:

| Compound | Structural formula | ¹H NMR and MS data |
|---|---|---|
| HD 22 | | ¹H NMR (300 MHz, CDCl$_3$) δ 9.64 (s, 1H), 7.88 (d, J = 3.3 Hz, 1H), 7.64 (t, J = 6.0 Hz, 1H), 7.44 (d, J = 3.3 Hz, 1H), 3.55-3.42 (m, 3H), 2.55 (t, J = 7.2 Hz, 2H), 1.73-1.66 (m, 4H), 1.33-1.28 (m, 2H), 0.83-0.77 (m, 2H) ESIMS (m/z): 441.0 [M + Na$^+$] |
| HD 26 | | ¹H NMR (300 MHz, CDCl$_3$) δ 7.86 (d, J = 3.3 Hz, 1H), 7.51 (s, 1H), 7.45 (d, J = 3.3 Hz, 1H), 6.05 (s, 2H), 3.57 (q, J = 12.0 Hz, 2H), 3.41-3.34 (m, 1H), 2.46 (t, J = 7.8 Hz, 2H), 1.76-1.63 (m, 4H), 1.34-1.28 (m, 2H), 0.83-0.79 (m, 2H) ESIMS (m/z): 440.1 [M + Na$^+$] |
| HD 27 | | ¹H NMR (300 MHz, CDCl$_3$) δ 7.85 (d, J = 3.0 Hz, 1H), 7.47 (s, 1H), 7.44 (d, J = 3.0 Hz, 1H), 3.47-3.43 (m, 3H), 2.50 (t, J = 7.2 Hz, 2H), 2.05 (s, 3H), 1.87 (s, 3H), 1.65-1.60 (m, 4H), 1.34-1.28 (m, 2H), 0.82-0.79 (m, 2H) ESIMS (m/z): 480.1 [M + Na$^+$] |
| HD 32 | | ¹H NMR (300 MHz, CDCl$_3$) δ 7.86 (d, J = 3.3 Hz, 1H), 7.45 (d, J = 3.3 Hz, 1H), 7.37-7.26 (m, 3H), 7.15 (t, J = 4.5 Hz, 1H), 6.76 (d, J = 7.2 Hz, 2H), 3.42-3.39 (m, 1H), 3.32 (q, J = 6.6 Hz, 2H), 2.46 (t, J = 7.5 Hz, 2H), 1.63-1.53 (m, 4H), 1.46-1.29 (m, 2H), 0.84-0.78 (m, 2H) ESIMS (m/z): 501.1 [M + Na$^+$] |
| HD 33 | | ¹H NMR (300 MHz, CDCl$_3$) δ 7.86 (d, J = 3.3 Hz, 1H), 7.44 (d, J = 3.3 Hz, 1H), 7.41 (s, 1H), 7.19-7.13 (m, 3H), 6.77 (t, J = 7.2 Hz, 1H), 6.65 (d, J = 8.4 Hz, 2H), 6.16 (t, J = 6.9 Hz, 1H), 3.49-3.41 (m, 3H), 2.20-2.13 (m ,2H), 1.82-1.70 (m, 2H), 1.37-1.29 (m, 2H), 0.88-0.80 (m, 2H) ESIMS (m/z): 501.1 [M + Na$^+$] |
| HD 45 | | ¹H NMR (300 MHz, CDCl$_3$) δ 8.90 (s, 1H), 7.85 (d, J = 3.3 Hz, 1H), 7.59 (s, 1H), 7.44 (d, J = 3.3 Hz, 1H), 3.57-3.55 (m, 3H), 2.52 (t, J = 8.1 Hz, 2H), 1.80-1.72 (m, 4H), 1.52 (s, 9H), 1.36-1.31 (m, 2H), 0.86-0.79 (m, 2H) ESIMS (m/z): 540.4 [M + Na$^+$] |

-continued

| Compound | Structural formula | ¹H NMR and MS data |
|---|---|---|
| HD 63 | | ¹H NMR (300 MHz, CDCl₃) δ 7.86 (d, J = 3.3 Hz, 1H), 7.52 (s, 1H), 7.45 (d, J = 3.3 Hz, 1H), 6.14 (d, J = 3.9 Hz, 1H), 3.55 (q, J = 6.3 Hz, 2H), 3.49-3.44 (m, 1H), 3.05 (d, J = 3.9 Hz, 3H), 2.41 (t, J = 8.1 Hz, 2H), 1.74-1.63 (m, 4H), 1.36-1.28 (m, 2H), 0.86-0.81 (m, 2H) ESIMS (m/z): 432.0 [M + H⁺] |
| HD 35 | | ¹H NMR (300 MHz, CDCl₃) δ 10.54 (s, 1H), 7.92 (d, J = 8.4 Hz, 2H), 7.84 (d, J = 3.3 Hz, 1H), 7.64 (t, J = 6.3 Hz, 1H), 7.52-7.36 (m, 3H), 7.47 (d, J = 3.3 Hz, 1H), 3.60 (t, J = 5.7 Hz, 2H), 2.74 (t, J = 7.8 Hz, 2H), 1.78-1.72 (m, 4H), 0.90-0.83 (m, 2H), 0.79-0.66 (m, 2H) ESIMS (m/z): 544.2 [M + Na⁺] |
| HD 36 | | ¹H NMR (300 MHz, CDCl₃) δ 10.79 (brs, 1H), 8.70 (d, J = 5.4 Hz, 2H), 7.84 (d, J = 3.3 Hz, 1H), 7.74 (d, J = 5.4 Hz, 2H), 7.72 (s, 1H), 7.43 (d, J = 3.3 Hz, 1H), 3.61 (t, J = 6.0 Hz, 2H), 3.58-3.48 (m, 1H), 2.78 (t, J = 6.6 Hz, 2H), 1.77-1.68 (m, 4H), 1.36-1.28 (m, 2H), 0.86-0.76 (m, 2H) ESIMS (m/z): 523.2 [M + H]⁺ |
| HD 40 | | ¹H NMR (300 MHz, CDCl₃) δ 10.77 (s, 1H), 9.11 (s, 1H), 8.70 (d, J = 3.6 Hz, 1H), 8.20 (d, J = 6.9 Hz, 1H), 7.85 (d, J = 3.3 Hz, 1H), 7.2 (t, J = 6.6 Hz, 1H), 7.44 (d, J = 3.3 Hz, 1H), 7.35 (dd, J = 6.9 Hz, J = 3.6 Hz, 1H), 3.64-3.50 (m, 3H), 2.76 (t, J = 7.8 Hz, 2H), 1.78-1.63 (m, 4H), 1.33-1.25 (m, 2H), 0.89-0.80 (m, 2H) ESIMS (m/z): 523.1 [M + H⁺] |

-continued

| Compound | Structural formula | ¹H NMR and MS data |
|---|---|---|
| HD 41 | | ¹H NMR (300 MHz, CDCl₃) δ 11.22 (s, 1H), 8.52 (dd, J = 7.8 Hz, J = 1.5 Hz, 1H), 8.20 (d, J = 7.8 Hz, 1H), 7.85 (d, J = 1.5 Hz, 1H), 7.82 (d, J = 3.3 Hz, 1H), 7.50 (t, J = 5.7 Hz, 1H), 7.46-7.42 (m, 1H), 7.40 (d, J = 3.3 Hz, 1H), 3.55 (t, J = 6.3 Hz, 2H), 3.41-3.39 (m, 1H), 2.66 (t, J = 7.2 Hz, 2H), 1.87-1.82 (m, 4H), 1.32-1.25 (m, 2H), 0.84-0.76 (m, 2H)<br>ESIMS (m/z): 545.0 [M + Na⁺] |
| HD 37 | | ¹H NMR (300 MHz, CDCl₃) δ 10.09 (s, 1H), 7.85 (d, J = 3.3 Hz, 1H), 7.65 (s, 1H), 7.44 (d, J = 3.3 Hz, 1H), 3.69-3.58 (m, 1H), 3.55 (q, J = 6.6 Hz, 2H), 2.61 (t, J = 7.2 Hz, 2H), 2.27 (s, 3H), 1.77-1.72 (m, 4H), 1.73-1.70 (m, 2H), 1.40-1.33 (m, 2H), 0.83-0.76 (m, 2H)<br>ESIMS (m/z): 482.1 [M + Na⁺] |
| HD 46 | | ¹H NMR (300 MHz, CDCl₃) δ 10.68 (s, 1H), 7.85 (d, J = 3.3 Hz, 1H), 7.74 (s, 1H), 7.44 (d, J = 3.3 Hz, 1H), 4.48 (d, J = 4.5 Hz, 2H), 3.78-3.72 (m, 1H), 3.57 (dd, J = 11.4, 6.6 Hz, 2H), 3.12 (s, 1H), 2.68 (t, J = 8.4 Hz, 2H), 1.77-1.73 (m, 2H), 1.73-1.70 (m, 2H), 1.42-1.37 (m, 2h), 0.87-0.76 (m, 2H)<br>ESIMS (m/z): 498.0 [M + Na⁺] |
| HD 48 | | ¹H NMR (300 MHz, CDCl₃) δ 9.42 (s, 1H), 7.86 (d, J = 3.3 Hz, 1H), 7.65 (s, 1H), 7.45 (d, J = 3.3 Hz, 1H), 4.26 (q, J = 7.2 Hz, 2H), 3.61-3.55 (m, 3H), 2.62 (t, J = 8.4 Hz, 2H), 1.77-1.72 (m, 4H), 1.33 (t, J = 7.2 Hz, 3H), 1.33-1.28 (m, 2H), 0.85-0.78 (m, 2H)<br>ESIMS (m/z): 512.0 [M + Na⁺] |
| HD 49 | | ¹H NMR (300 MHz, CDCl₃) δ 9.82 (s, 1H), 7.85 (d, J = 3.0 Hz, 1H), 7.62 (s, 1H), 7.44 (d, J = 3.0 Hz, 1H), 3.79-3.69 (m, 1H), 3.56 (q, J = 5.4 Hz, 2H), 2.71-2.59 (m, 4H), 1.78-1.74 (m, 4H), 1.37-1.31 (m, 2H), 1.15 (t, J = 7.5 Hz, 3H), 0.86-0.78 (m, 2H)<br>ESIMS (m/z): 498.0 [M + Na⁺] |

| Compound | Structural formula | ¹H NMR and MS data |
|---|---|---|
| HD 50 | 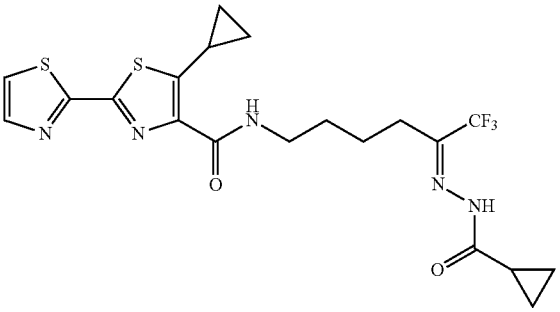 [SMILES: O=C(NCCCC/C(=N/NC(=O)C1CC1)C(F)(F)F)c1nc(-c2nccs2)sc1C1CC1] | ¹H NMR (300 MHz, CDCl₃) δ 9.87 (s, 1H), 7.86 (d, J = 3.3 Hz, 1H), 7.61 (s, 1H), 7.44 (d, J = 3.3 Hz, 1H), 3.57-3.40 (m, 3H), 2.62 (t, J = 8.7 Hz, 2H), 1.75-1.60 (m, 4H), 1.37-1.31 (m, 2H), 1.25-1.06 (m, 2H), 0.90-0.80 (m, 2H), 0.80-0.76 (m, 2H) ESIMS (m/z): 508.3 [M + Na⁺] |
| HD 51 | 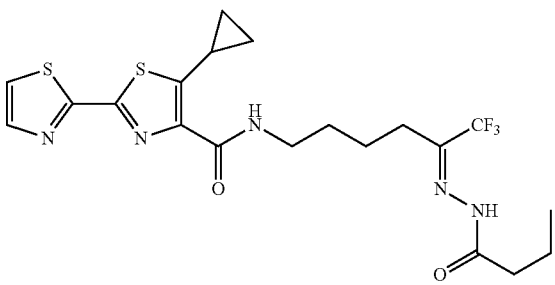 [SMILES: CCCC(=O)N/N=C(/CCCCNC(=O)c1nc(-c2nccs2)sc1C1CC1)C(F)(F)F] | ¹H NMR (300 MHz, CDCl₃) δ 9.89 (s, 1H), 7.85 (d, J = 3.0 Hz, 1H), 7.62 (s, 1H), 7.43 (d, J = 3.0 Hz, 1H), 3.68-3.60 (m, 1H), 3.55 (q, J = 5.4 Hz, 2H), 2.66-2.59 (m, 4H), 1.75-1.65 (m, 6H), 1.42-1.36 (m, 2H), 0.96 (t, J = 7.2 Hz, 3H), 0.86-0.79 (m, 2H) ESIMS (m/z): 510.1 [M + Na⁺] |
| HD 52 | 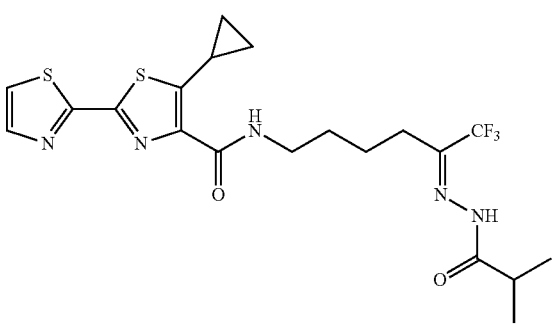 [SMILES: CC(C)C(=O)N/N=C(/CCCCNC(=O)c1nc(-c2nccs2)sc1C1CC1)C(F)(F)F] | ¹H NMR (300 MHz, CDCl₃) δ 9.73 (s, 1H), 7.85 (d, J = 3.3 Hz, 1H), 7.59 (s, 1H), 7.44 (d, J = 3.3 Hz, 1H), 3.54 (q, J = 5.7 Hz, 2H), 3.52-3.43 (m, 1H), 2.61 (t, J = 8.1 Hz, 2H), 1.80-1.72 (m, 4H), 1.38-1.33 (m, 2H), 1.15 (d, J = 6.9 Hz, 6H), 0.86-0.79 (m, 2H) ESIMS (m/z): 510.3 [M + Na⁺] |

BIOLOGICAL EXPERIMENTAL EXAMPLES

Experimental Example 1: Test for the Inhibition Activity Against Histone Deacetylase 1, 3, 4, 6 (HDAC1, 3, 4, 6)

1. Objective of the Test:

The test was carried out to show the inhibition activity of the compounds in this patent application against human source histone deacetylases 1, 3, 4, 6.

2. Materials for the Test:

Human source HDAC1, HDAC3, HDAC4, and HDAC6 were obtained by the Group of Doctor LI Jia in Shanghai Institute of Materia Medica by using the baculovirus expression system and purifying.

Substrate: HDAC1, 3, 4: Ac-Lys-Tyr-Lys (Ac)-AMC; HDAC6: Boc-lys (Ac)-AMC

∠All were purchased from GL Biochem (Shanghai) Ltd.;

3. Test Principle:

Enzyme activity was measured in 96-well or 384-well flat-bottom microplates using fluorescence detection. After the substrate was deacetylated by HDAC, it was hydrolyzed by trypsin to give a product of AMC which showed the fluorescence signal in the detection under 460 nm emission light excited by 355 nm of fluorescence detector. The initial reaction speed was calculated by detecting the changes of the fluorescence signal over time.

4. Experimental Process:

Sample treatment: The sample was dissolved in DMSO and stored at low temperature. The concentration of DMSO in the final system was controlled within a range that did not affect the detection of activity.

Illustration about the data processing and the result: In the first screening, the activity of the sample was tested at a single concentration, e.g., 20 μg/ml. For the samples exhibiting activity under certain conditions, for example, the inhibition ratio (%) was greater than 50, the activity-dose dependent relationship was tested, i.e., $IC_{50}/EC_{50}$ value was obtained by non-linearly fitting the sample activity to the sample concentration, the calculating software was Graphpad Prism 4, and the model used for fitting was sigmoidal dose-response (varible slope). The bottom and top of the fitting curve were set to 0 and 100 for the most inhibitor screening models. Under normal circumstances, multiple holes (n≥2) were set for each sample in the test, and the Standard Deviation (SD) or Standard Error (SE) was shown in the result. For each test, a listed compound SAHA (Vorinostat) was also tested as a control.

5. Test Results for Part of the Compounds:

TABLE 1

| ID | IC50: μM | | | |
|---|---|---|---|---|
| | HDAC1 | HDAC3 | HDAC4 | HDAC6 |
| SAHA | 0.13 ± 0.01 | 0.18 ± 0.04 | 0.20 ± 0.02 | 0.11 ± 0.01 |
| CFH367-C | 0.07 ± 0.01 | 0.26 ± 0.05 | 0.10 ± 0.01 | 0.79 ± 0.14 |
| HD 1 | 0.02 ± 0.00 | 0.02 ± 0.00 | 0.02 ± 0.00 | 0.50 ± 0.01 |
| HD 3 | 0.02 ± 0.00 | 0.02 ± 0.00 | 0.02 ± 0.00 | 0.91 ± 0.01 |
| HD 6 | 0.06 ± 0.01 | 0.04 ± 0.00 | 0.04 ± 0.00 | 0.55 ± 0.09 |
| HD 53 | 0.05 ± 0.00 | 0.05 ± 0.00 | 0.04 ± 0.00 | 0.04 ± 0.00 |
| HD 55 | 0.03 ± 0.00 | 0.03 ± 0.00 | 0.07 ± 0.00 | 0.02 ± 0.00 |
| HD 54 | 0.07 ± 0.01 | 0.06 ± 0.00 | 0.07 ± 0.00 | 0.06 ± 0.00 |
| HD 37 | 0.18 ± 0.03 | 0.35 ± 0.00 | 0.16 ± 0.01 | 0.08 ± 0.01 |
| HD 46 | 0.50 ± 0.05 | 0.40 ± 0.01 | 0.45 ± 0.03 | 0.35 ± 0.01 |

From the experimental results in above table 1, it can be seen that the activity of each HDAC hypotype is increased several times when the site R4 is changed, i.e., the previous hydroxamic acid for CFH467-C is changed to trifluoroacetyl ketones. Wherein, HD 1 has a very high inhibition activity against HDAC1, 3, 4, $IC_{50}$ can reach about 20 nM; and the activity against HDAC6 can be improved when trifluoroacetyl ketone is further modified into hydrazone compounds (HD 37, HD 46). And a good inhibition activity against HDAC was shown no matter the thiazole ring was substituted with alkyl or aryl groups.

Experimental Example 2: Anti-tumor Activity Test in Cellular Level

1. Objective of the Test:

The antitumor activity of the compounds of the present invention was tested, the in vitro antitumor activity of the compounds were evaluated by measuring the inhibition activity of the compounds against the growth of human source multiple myeloma cell line 8266.

2. Materials for the Test:

Human source multiple myeloma cell line 8266 was gifted by Dr. HOU Jian in Shanghai Changzheng Hospital.

3. Test Principle:

Tetrazolium salts (MTT) colorimetry was used, the analytic method is based on the metabolic reduction of 3-(4,5-dimethyl-2-thiazolyl)-2,5-diphenyltetrazolium bromide (MTT). The NADP-related dehydrogenase existing in the mitochondria of living cells can reduce the yellow MTT to insoluble bluish violet Formazan, but the enzyme is disappeared in dead cells and MTT cannot be reduced. The optical density was measured at a wavelength of 550/690 nm using a microplate reader after Formazan was dissolved in DMSO.

4. Experimental Process:

Sample treatment: The sample was dissolved in DMSO and stored at low temperature. The concentration of DMSO in the final system was controlled within a range that did not affect the detection of activity.

The cell viability was measured by MTT assay. Cells in logarithmic growth phase were digested with 0.05% trypsin and cell numbers were counted, then 100 μL was inoculated in 96-well plate at a cell density of 2.0×10³/well, and the plate was placed in an incubator with 5% $CO_2$ at 37° C. overnight. Six concentration gradients were set up for each compound and three wells were set for each concentration. The compound of each concentration was added to the corresponding wells, and incubated at 37° C. in an incubator with 5% $CO_2$ for 72 hours, and then 20 μL of 5 mg/mL MTT was added to each well. After incubation for 3 hours at 37° C., the supernatant was discarded, the remained was added with 100 μL of DMSO to be dissolved, the absorbing value was measured at the light of 550 nm (L1) using a Spectra-MAX 340, and the reference wavelength was 690 nm (L2). The value of (L1-L2) was plotted against the concentration of inhibiting agent, and the $IC_{50}$ was obtained by fitting the formula.

Illustration about the data processing and the result: in the first screening, the activity of the sample was tested at a single concentration, e.g., 20 μg/ml. For the samples exhibiting activity under certain conditions, for example, the inhibition ratio (%) was greater than 50, the activity-dose dependent relationship was tested, i.e., $IC_{50}/EC_{50}$ value, was obtained by non-linearly fitting the sample activity to the sample concentration, the calculating software was Graphpad Prism 4, and the model used for fitting was sigmoidal dose-response (varible slope). The bottom and top of the fitting curve were set to 0 and 100 for the most inhibitor screening models. Under normal circumstances, multiple holes (n≥2) were set for each sample in the test, the Standard Deviation (SD) or Standard Error (SE) was shown in the result (it was IC50±SD in the table). For each test, a listed compound SAHA (Vorinostat) was also tested as a control.

4. Test Results for Part of the Compounds:

Activity Results on human multiple myeloma cell line 8266:

TABLE 2

| ID | $IC_{50}(\mu M)$ | ID | $IC_{50}(\mu M)$ |
|---|---|---|---|
| SAHA | 2.466 ± 0.024 | CFH367-C | 1.139 ± 0.149 |
| HD 1 | 0.333 ± 0.011 | HD 46 | 0.117 ± 0.026 |
| HD 3 | 0.240 ± 0.021 | HD 6 | 0.457 ± 0.012 |
| HD 37 | 2.140 ± 0.022 | | |

As can be seen from the above table, the compounds described in the present patent application also exhibit a good inhibition activity against tumor cell proliferation, the activity at the cellular level (HD 46: $IC_{50}$=0.117 μM) was increased about 10 times compared to the previously reported compound CFH367-C ($IC_{50}$=1.139 μM), and the activity of the compound on the cell was essentially consistent with the activity on the enzyme.

Experimental Example 3: Test of Drug Efficacy of Compounds in EAE Mouse Models

1. Objective of the Test:

The activity of the compound as a histone deacetylase inhibitor in the treatment of EAE was tested by drug efficacy tests for compounds in the EAE mouse model.

Antigen MOG35-55 (MEVGWYRSPFSRVVH-LYRNGK) was added with complete Freund's adjuvant (comprising 5 mg/ml of inactivated *Mycobacterium tuberculosis*) to be emulsified. 8-week aged female C57BL/6 mouse was injected subcutaneously with 200 μg of emulsified MOG35-55 antigen, while 200 ng of pertussis toxin was injected into each mouse. The day of induction was day 0. On day 2, 200 ng of pertussis toxin was further injected to each mouse. The symptoms of the mice were scored and recorded daily. The scoring rules were as follows, 0 point: normal, asymptomatic 0.5 points: the tail tip was weak and could not be erected 1 point: the entire tail was completely weak, 2 points: hind limb was weak. The mouse was hung upside down on the edge of the cage by one hind limb alone, if the hind limb was weak, the mouse can not grasp the edge of the cage, and thus cannot climb back into the cage and fall from the edge of the cage, the case that one hind limb was weak was scored of 1.5 points, that both hind limbs were weak was scored of 2 points.

3 points: the mouse was paralysis of hind limbs, and the mouse was loss of mobility.

4 points: the mouse was weakness or paralysis of forelimbs.

5 points: the mouse was dead or dying

2. Materials for the Test:
EAE mouse: Shanghai Slac Laboratory Animal Co., Ltd.;
Antigen MOG35~55: GL Biochem (Shanghai) Ltd.;

3. Test Method:
HD 1 was in a pure compound form, while CFH367-C was the control group. The drug was directly added with the CMC—Na, ground and ultrasonic suspended into a uniform state. The dose was 10 mg/kg, twice a day by intragastric administration. The control group was directly administrated with PBS.

4. Test Results:
HDACi HD 1 can Effectively Reduce the Incidence of EAE Model Mice.

From the incidence rate and incidence curves (the FIGURE), it can be seen that HDAC inhibitor HD 1 shows a good therapeutic effect on the clinical symptoms of EAE model mice, and the effect is better than CFH367-C. The disease severity of the mice in the treatment group was significantly lower than the solvent control group (P<0.01).

Incidence rate:

|  | Incidence number/total number |
|---|---|
| Blank control | 6/6 |
| HD 1 | 3/6 |
| CFH367-C | 5/6 |

The invention claimed is:

1. A 2,2'-bis-thiazole-based compound represented by formula I:

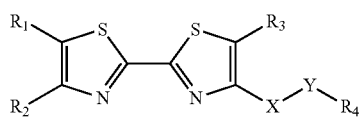

Formula I wherein,
$R_1$ and $R_2$ are each independently selected from the group consisting of H, $C_3$-$C_6$ cycloalkyl, $C_1$-$C_6$ alkyl, $C_2$-$C_6$ alkenyl and $C_2$-$C_6$ alkynyl; or $R_1$ and $R_2$ together with the carbon atoms to which they are attached form a 5- to 7-membered cyclic structure;

X is

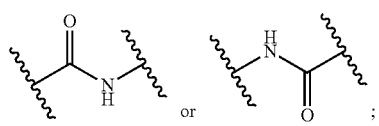 [SMILES: *NC(*)=O ; *NC(*)=O]

Y is

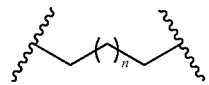

or $C_2$-$C_6$ alkenylene, wherein n is 1, 2, 3 or 4;

$R_3$ is selected from the group consisting of H, $C_1$-$C_6$ alkyl, $C_1$-$C_6$ alkyl substituted with $C_6$-$C_{10}$ aryl, $C_3$-$C_6$ cycloalkyl, $C_3$-$C_6$ cycloalkyl substituted with $C_1$-$C_6$ alkyl, $C_2$-$C_8$ alkenyl, $C_2$-$C_6$ alkynyl, $C_6$-$C_{10}$ aryl, and 5- to 7-membered heteroaryl; the 5- to 7-membered heteroaryl contains 1 to 3 heteroatoms selected from N, O and S; and $R_4$ is $R_{4a}$, $R_{4b}$, $R_{4c}$, $R_{4d}$ or $R_{4e}$:

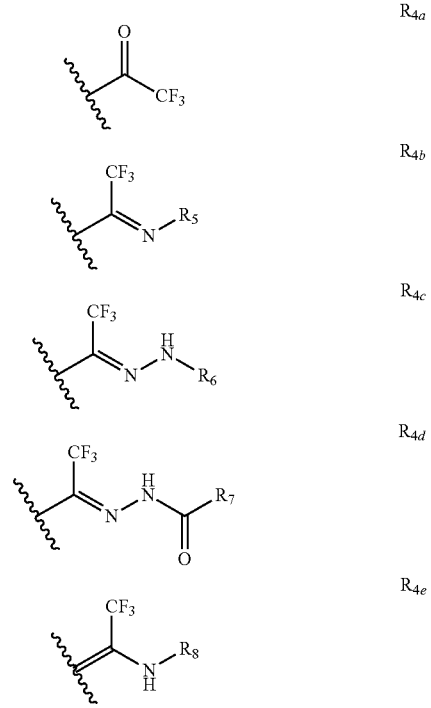

wherein $R_5$, $R_6$, $R_7$ and $R_8$ are selected from the group consisting of H, hydroxyl, $C_1$-$C_6$ alkyl, $C_1$-$C_6$ alkoxy, hydroxyl ($C_1$-$C_6$) alkylene, $C_1$-$C_6$ alkyl substituted with $C_6$-$C_{10}$ aryl, $C_3$-$C_6$ cycloalkyl, $C_3$-$C_6$ cycloalkyl substituted with $C_1$-$C_6$ alkyl, $C_2$-$C_8$ alkenyl, $C_2$-$C_6$ alkynyl, $C_6$-$C_{10}$ aryl, 5- to 7-membered heteroaryl, and

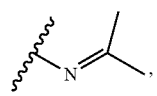

the 5- to 7-membered heteroaryl contains 1 to 3 heteroatom(s) selected from N, O and S.

2. The 2,2'-bis-thiazole-based compound according to claim 1, wherein,
$R_1$ and $R_2$ are each independently H or $C_1$-$C_6$ alkyl; or $R_1$ and $R_2$ together with the carbon atoms to which they are attached form a 5-, 6- or 7-membered saturated cyclic structure;

Y is

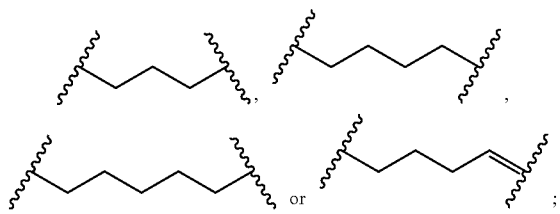

R$_3$ is C$_1$-C$_4$ alkyl, C$_1$-C$_4$ alkyl substituted with C$_6$-C$_{10}$ aryl, or C$_3$-C$_6$ cycloalkyl;

R$_5$ is hydroxyl, C$_1$-C$_6$ alkyl, C$_1$-C$_6$ alkoxy, C$_6$-C$_{10}$ aryl, or

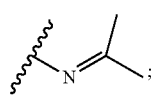 [SMILES: *N=C(C)C]

R$_6$ is H or C$_1$-C$_6$ alkyl;

R$_7$ is C$_1$-C$_6$ alkyl, C$_3$-C$_6$ cycloalkyl, C$_1$-C$_6$ alkoxy, hydroxyl (C$_1$-C$_6$) alkylene, C$_6$-C$_{10}$ aryl or 5- to 7-membered heteroaryl, the 5- to 7-membered heteroaryl contains 1 to 3 heteroatom(s) selected from N, O and S; and R$_8$ is C$_6$-C$_{10}$ aryl.

3. The 2,2'-bis-thiazole-based compound according to claim 2, wherein,

R$_3$ is C$_1$-C$_4$ alkyl, benzyl, or cyclopropyl;

R$_5$ is hydroxyl, C$_1$-C$_4$ alkyl, C$_1$-C$_4$ alkoxy, phenyl, or

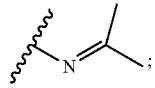

R$_6$ is H or methyl;

R$_7$ is C$_1$-C$_4$ alkyl, C$_3$-C$_5$ cycloalkyl, C$_1$-C$_4$ alkoxy, hydroxy C$_1$-C$_4$ alkylene, C$_6$-C$_{10}$ aryl or 5- to 7-membered heteroaryl, the 5- to 7-membered heteroaryl contains 1-2 heteroatom(s) selected from N, O and S; and R$_8$ is phenyl.

4. The 2,2'-bis-thiazole-based compound according to claim 3, wherein R$_7$ is methyl, ethyl, propyl, isopropyl, tert-butyl, cyclopropyl, methoxy, ethyloxy, hydroxymethyl, hydroxyethyl, phenyl, pyridinyl, pyridazinyl, pyrimidinyl or pyrazinyl.

5. The 2,2'-bis-thiazole-based compound according to claim 1, wherein the 2,2'-bis-thiazole-based compound is selected from the following compounds:

HD 1

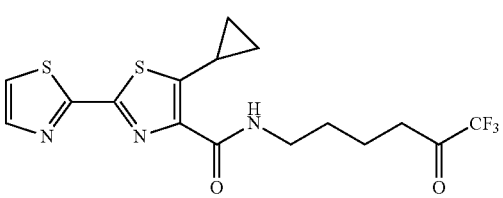

HD 3

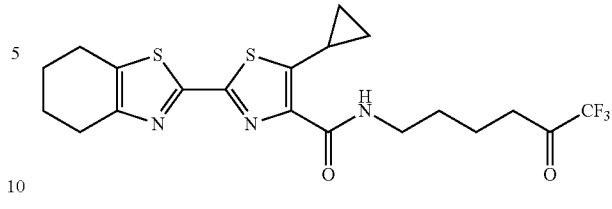

HD 6

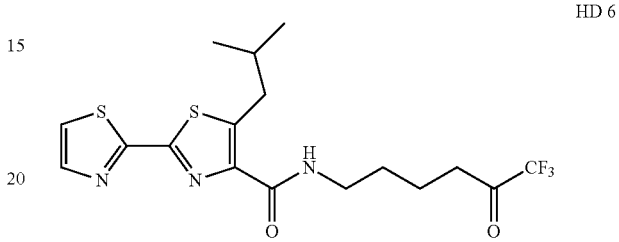

HD 17

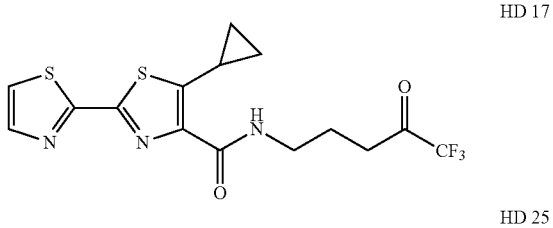

HD 25

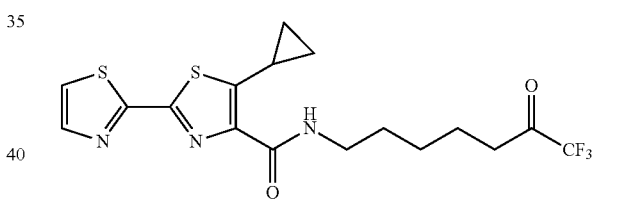

HD 53

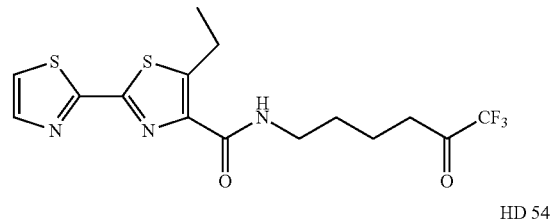

HD 54

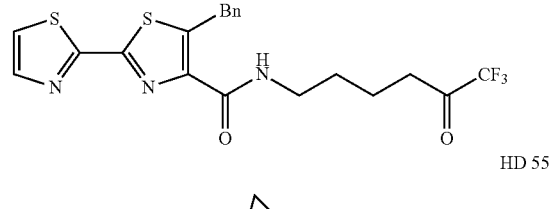

HD 55

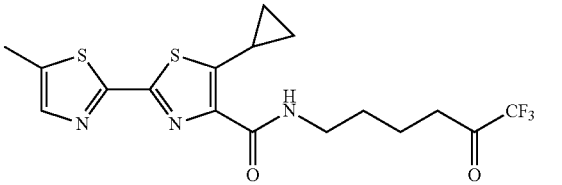

HD 60
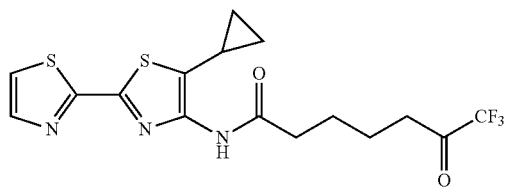
HD 22
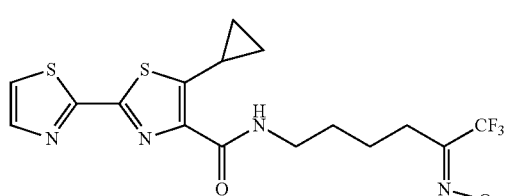
HD 26
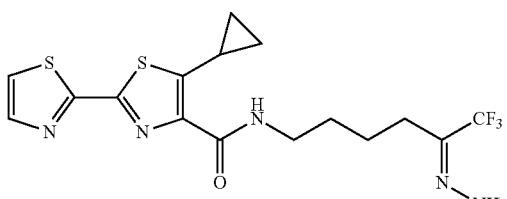
HD 27
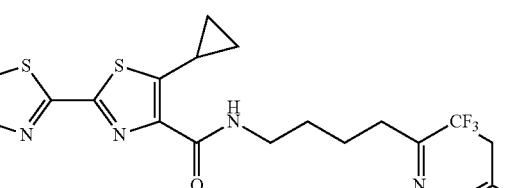
HD 32
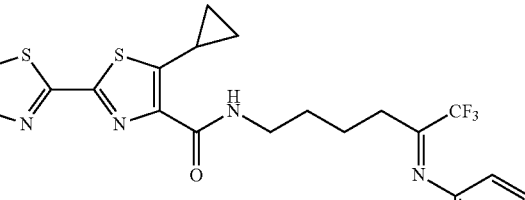
HD 33
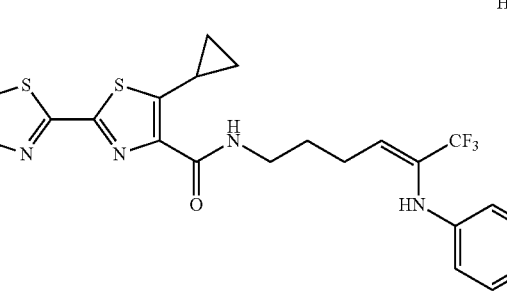
HD 45
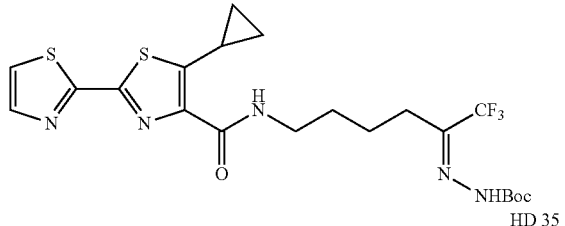
HD 35
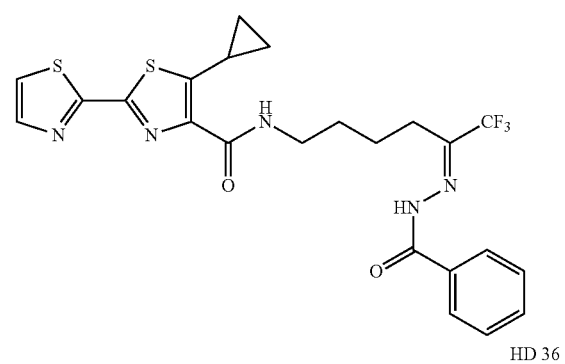
HD 36
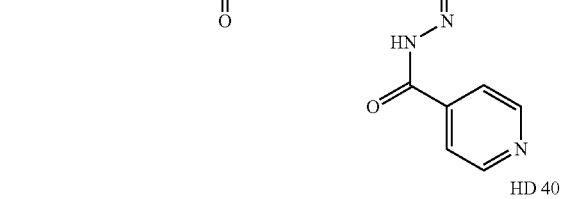
HD 40
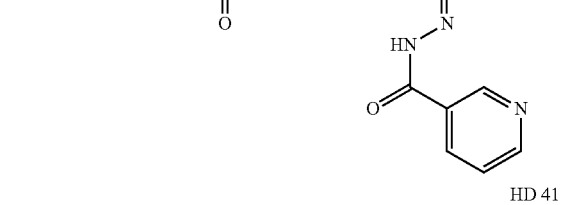
HD 41

41
-continued
HD 37
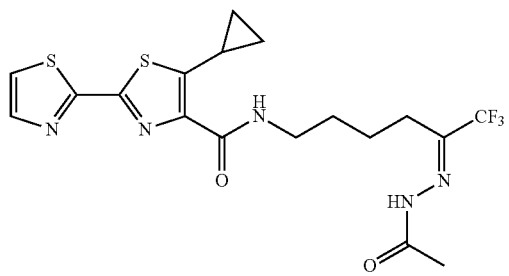
HD 46
HD 48
HD 49
HD 50
42
-continued
HD 51
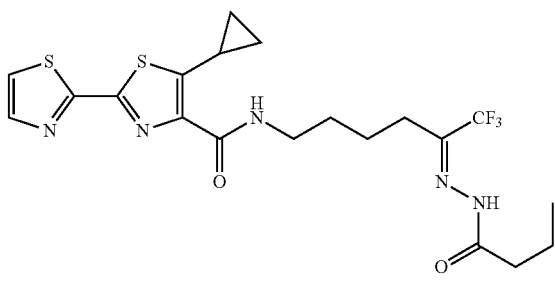
HD 52
and
HD 63
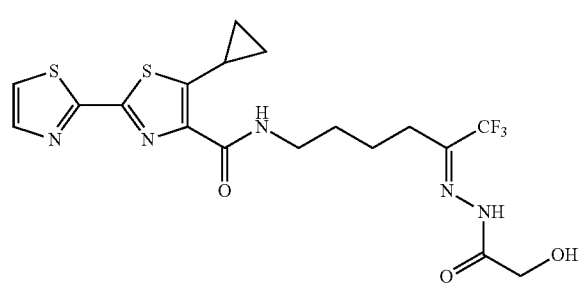
6. A process for preparing the 2,2'-bis-thiazole-based compound according to claim 1, the process comprising, obtaining compound $I_a$ by Route I,
Route I
wherein definitions of $R_1$, $R_2$, $R_3$ and n are the same as defined in the formula I in claim 1, by converting compound 1 to acyl chloride using an acyl chloride reagent;
subjecting the acyl chloride to a substitution reaction with TFAA in the presence of a base at room temperature or under heating; and hydrolyzing a resultant of the substitution reaction to form the compound Ia;
preparing compound $I_b$ by Route IV:

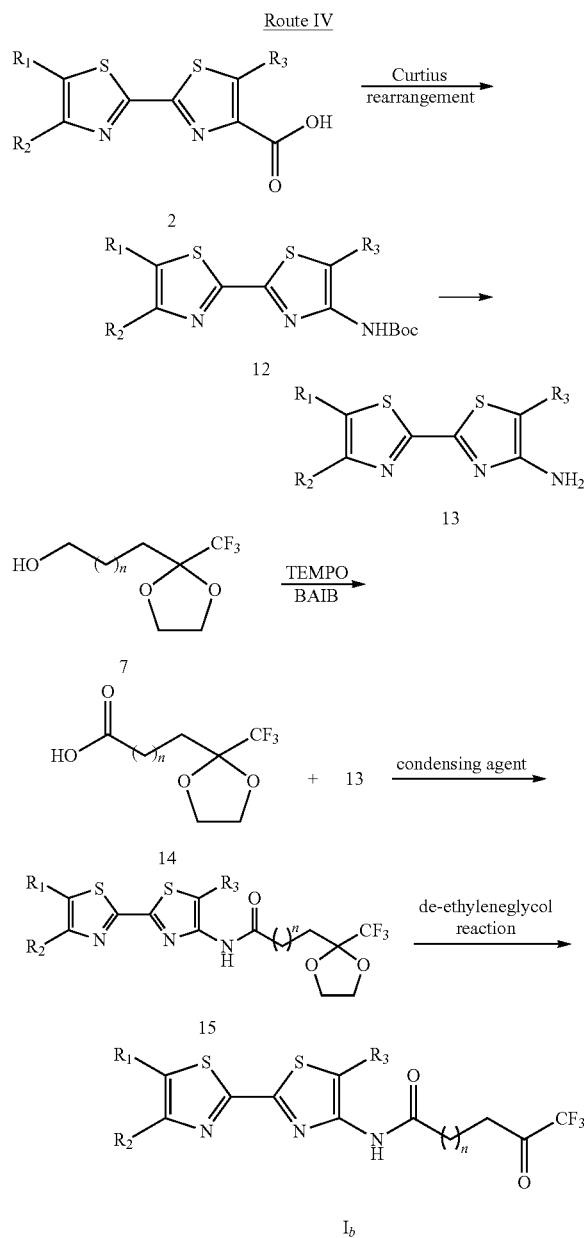

wherein definitions of $R_1$, $R_2$, $R_3$ and n are the same as defined in the formula I in claim 1,
by subjecting compound 2 to a Curtius rearrangement reaction to form a Boc-protected amine 12;
removing a Boc-group from compound 12 to form a free amine 13;
oxidizing compound 7 by TEMPO and BAIB to form acid 14;
reacting the acid 14 with the amine 13 under a condensing agent to form compound 15; and subjecting the compound 15 to a de-ethyleneglycol reaction under a Lewis acid to form the compound $I_b$; or
preparing compound $I_c$ by Route V:

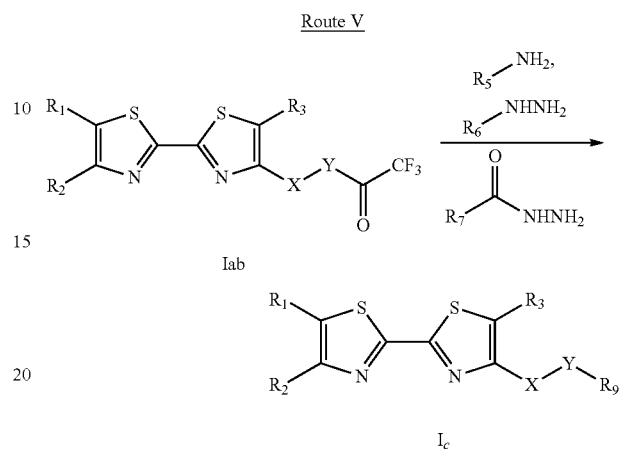

wherein definitions of $R_1$, $R_2$, $R_3$, $R_5$, $R_6$, $R_7$, X and Y are the same as defined in the formula I in claim 1 and $R_9$ is one selected from $R_{4b}$, $R_{4c}$ and $R_{4d}$,
subjecting compound $I_{ab}$ to a dehydration condensation reaction with

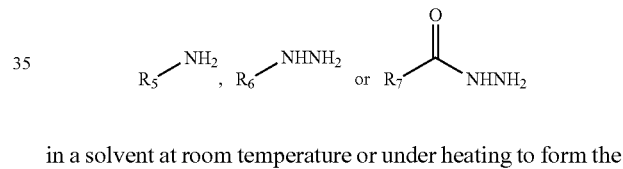

in a solvent at room temperature or under heating to form the compound $I_c$.

7. A pharmaceutical composition comprising a therapeutically effective amount of one or more 2,2'-bis-thiazole-based compounds represented by the formula I according to claim 1 and a pharmaceutically acceptable excipient.

8. A process for preparing the 2,2'-bis-thiazole-based compound according to claim 1, the process comprising,
obtaining compound $I_a$ by Route II,

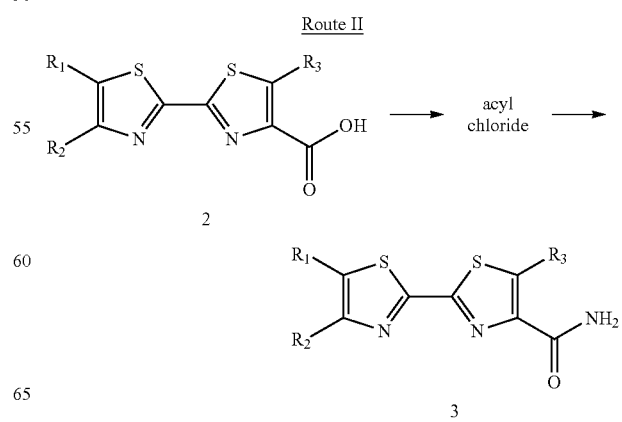

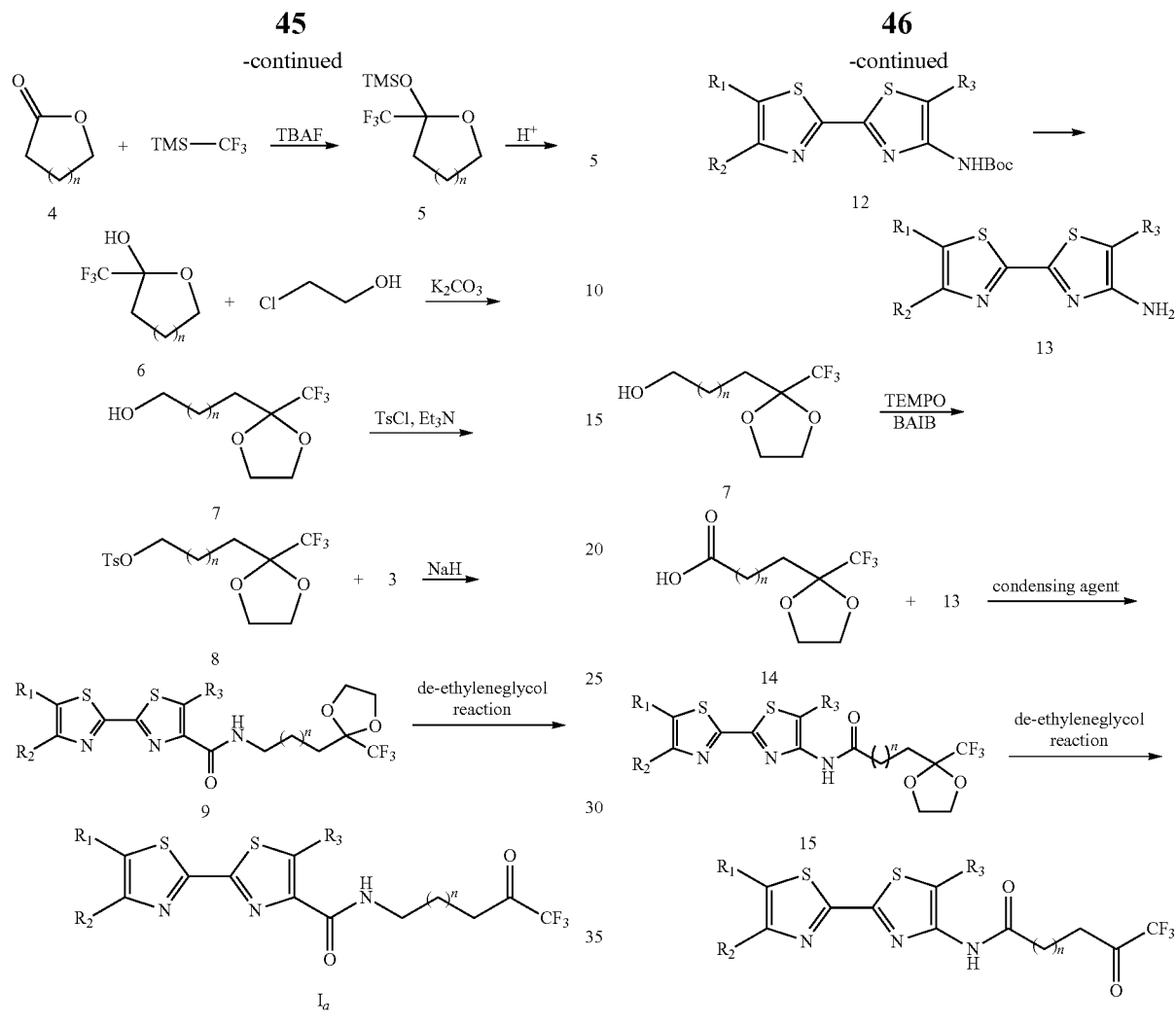

wherein definitions of $R_1$, $R_2$, $R_3$ and n are the same as defined in the formula I in claim 1, by converting compound 2 to acyl chloride using an acyl chloride reagent;

reacting the acyl chloride with concentrated ammonia water under an ice bath to form compound 3;

subjecting compound 4 to an additive reaction with TMS-$CF_3$ under a catalyst of TBAF in tetrahydrofuran to form compound 5;

hydrolyzing compound 5 with $H^+$ to form compound 6;

reacting the compound 6 with 2-chloroethanol in DMF in a presence of $K_2CO_3$ to form compound 7;

sulfonylating compound 7 in DCM in a presence of TsCl and $Et_3N$ to form compound 8;

reacting the compound 8 with the compound 3 under sodium hydride in DMF to form compound 9; or subjecting the compound 9 to a de-ethyleneglycol reaction under a Lewis acid to form the compound Ia;

preparing compound $I_b$ by Route IV:

Route IV $2 \xrightarrow{\text{Curtius rearrangement}}$ wherein definitions of $R_1$, $R_2$, $R_3$ and n are the same as defined in the formula I in claim 1, subjecting compound 2 to a Curtius rearrangement reaction to form a Boc-protected amine 12;

removing a Boc-group from compound 12 to form a free amine 13;

oxidizing compound 7 by TEMPO and BAIB to form acid 14;

reacting the acid 14 with the amine 13 under a condensing agent to form compound 15; and subjecting the compound 15 to a de-ethyleneglycol reaction under a Lewis acid to form the compound $I_b$; or preparing compound $I_c$ by Route V:

Route V

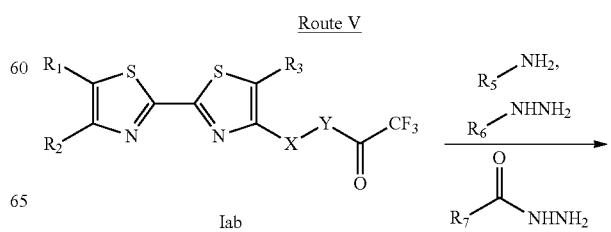

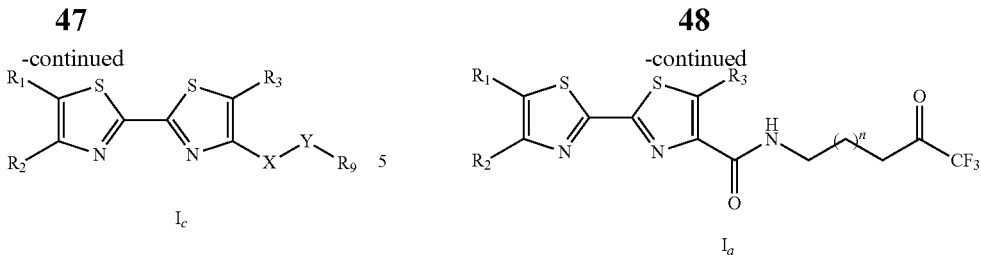

wherein definitions of $R_1$, $R_2$, $R_3$, $R_5$, $R_6$, $R_7$, X and Y are the same as defined in the formula I in claim 1 and $R_9$ is one selected from $R_{4b}$, $R_{4c}$ and $R_{4d}$, subjecting compound $I_{ab}$ to a dehydration condensation reaction with

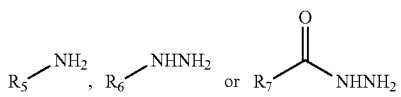

in a solvent at room temperature or under heating to form the compound $I_c$.

9. A process for preparing the 2,2'-bis-thiazole-based compound according to claim 1, the process comprising, obtaining compound $I_a$ by Route III, wherein definitions of $R_1$, $R_2$, $R_3$ and n are the same as defined in the formula I in claim 1, by reacting compound 8 with $NaN_3$ in DMF to form compound 10;

reducing compound 10 by hydrogenation to form amine 11;

subjecting the amine 11 to a condensation reaction with acid 2 in a presence of a condensing agent in DCM to form compound 9;

subjecting the compound 9 to a de-ethyleneglycol reaction under a Lewis acid to form the compound Ia;

preparing compound $I_b$ by Route IV:

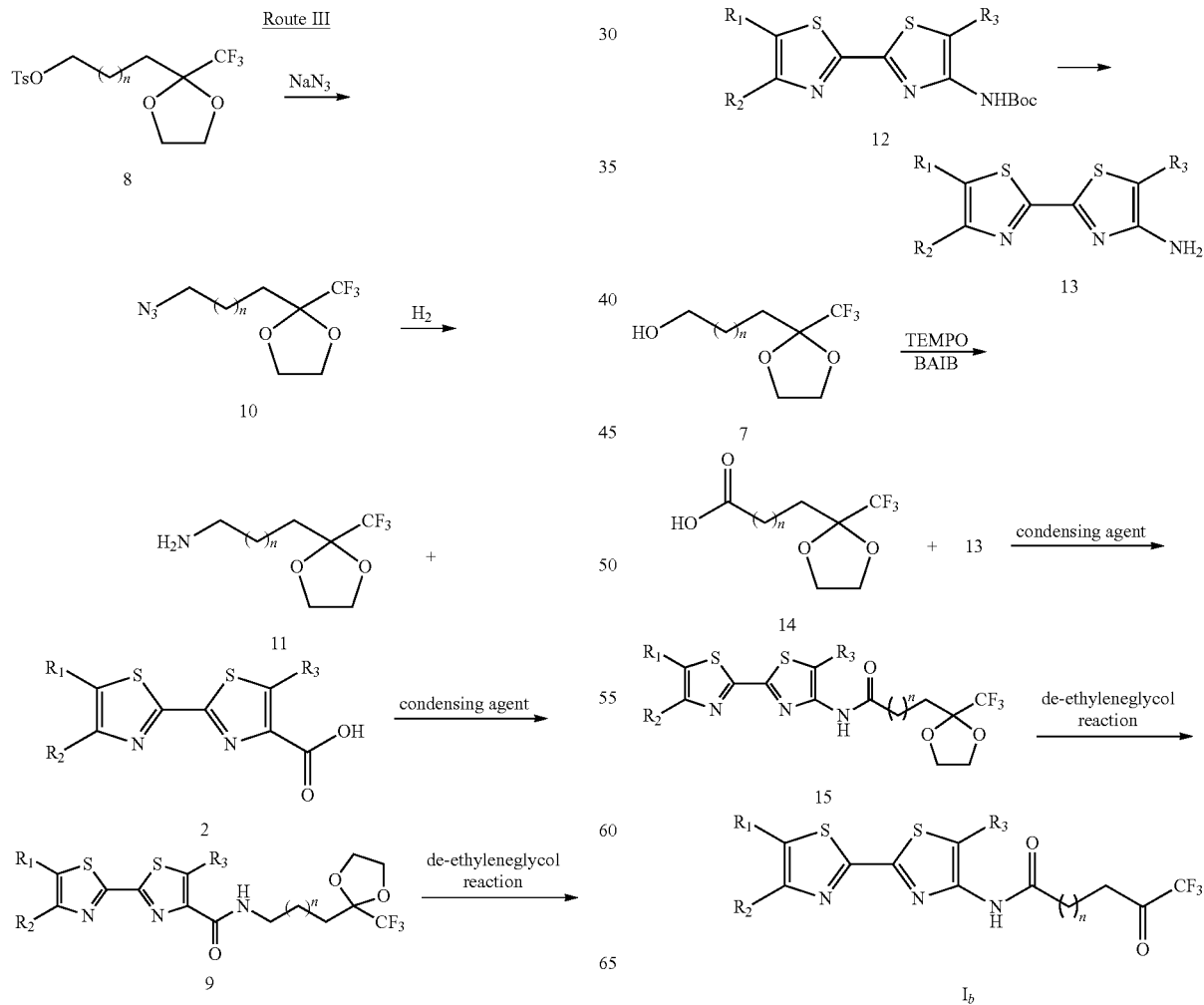

wherein definitions of $R_1$, $R_2$, $R_3$ and n are the same as defined in the formula I in claim 1, subjecting compound 2 to a Curtius rearrangement reaction to form a Boc-protected amine 12;

removing a Boc-group from compound 12 to form a free amine 13;

oxidizing compound 7 by TEMPO and BAIB to form acid 14;

reacting the acid 14 with the amine 13 under a condensing agent to form compound 15; and subjecting the compound 15 to a de-ethyleneglycol reaction under a Lewis acid to form the compound $I_b$; or preparing compound $I_c$ by Route V:

Route V

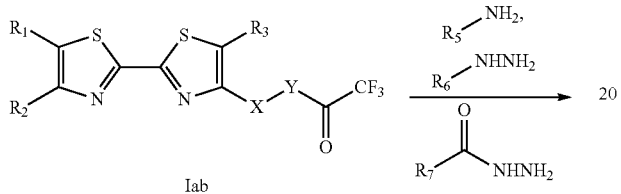

Iab

-continued

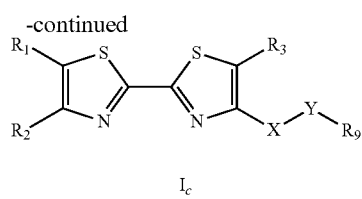

$I_c$ wherein definitions of $R_1$, $R_2$, $R_3$, $R_5$, $R_6$, $R_7$, X and Y are the same as defined in the formula I in claim 1 and $R_9$ is one selected from $R_{4b}$, $R_{4c}$ and $R_{4d}$, subjecting compound $I_{ab}$ to a dehydration condensation reaction with

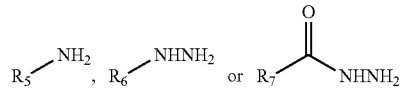

in a solvent at room temperature or under heating to form the compound $I_c$.

* * * * *